US010585088B2

(12) United States Patent
Gohel et al.

(10) Patent No.: US 10,585,088 B2
(45) Date of Patent: Mar. 10, 2020

(54) STABLE NANOMAGNETIC PARTICLE DISPERSIONS

(71) Applicant: BioLegend, Inc., San Diego, CA (US)

(72) Inventors: Dhanesh Gohel, San Diego, CA (US); Hong Zhang, La Jolla, CA (US); John Ransom, Encinitas, CA (US)

(73) Assignee: BioLegend, Inc., San Diego, CA (US)

( * ) Notice: Subject to any disclaimer, the term of this patent is extended or adjusted under 35 U.S.C. 154(b) by 0 days.

(21) Appl. No.: 15/143,552

(22) Filed: Apr. 30, 2016

(65) Prior Publication Data

US 2016/0320376 A1    Nov. 3, 2016

Related U.S. Application Data

(60) Provisional application No. 62/156,141, filed on May 1, 2015.

(51) Int. Cl.
  *G01N 33/543*    (2006.01)
  *G01N 33/552*    (2006.01)

(52) U.S. Cl.
  CPC ..... *G01N 33/54326* (2013.01); *G01N 33/552* (2013.01)

(58) Field of Classification Search
  CPC ....... G01N 33/54326; G01N 33/57492; G01N 33/552; G01N 2333/70514
  See application file for complete search history.

(56) References Cited

U.S. PATENT DOCUMENTS

| | | |
|---|---|---|
| 3,933,997 A | 1/1976 | Hersh et al. |
| 4,169,804 A | 10/1979 | Yapel, Jr. |
| 4,177,253 A | 12/1979 | Davies et al. |
| 4,230,685 A | 10/1980 | Senyei et al. |
| 4,267,234 A | 5/1981 | Rembaum |
| 4,358,388 A | 11/1982 | Daniel et al. |
| 4,452,773 A | 6/1984 | Molday |
| 4,454,234 A | 6/1984 | Czerlinski |
| 4,554,088 A | 11/1985 | Whitehead et al. |
| 4,582,622 A | 4/1986 | Ikeda et al. |
| 4,654,267 A | 3/1987 | Ugelstad et al. |
| 4,695,392 A | 9/1987 | Whitehead et al. |
| 4,783,336 A | 11/1988 | Margel et al. |
| 4,795,698 A | 1/1989 | Owen et al. |
| 4,965,007 A | 10/1990 | Yudelson |
| 5,069,216 A | 12/1991 | Groman et al. |
| 5,091,206 A | 2/1992 | Wang et al. |
| 5,108,933 A | 4/1992 | Liberti et al. |
| 5,116,724 A | 5/1992 | Delaage et al. |
| 5,169,754 A | 12/1992 | Siiman et al. |
| 5,186,827 A | 2/1993 | Liberti et al. |
| 5,246,829 A | 9/1993 | Delaage et al. |
| 5,320,944 A | 6/1994 | Okada et al. |
| 5,385,707 A | 1/1995 | Miltenyi et al. |
| 5,411,730 A | 5/1995 | Kirpotin |
| 5,478,741 A * | 12/1995 | Maret .................. C07K 14/445 435/34 |
| 5,512,332 A | 4/1996 | Liberti et al. |
| 5,597,531 A | 1/1997 | Liberti et al. |
| 5,639,620 A | 6/1997 | Siiman et al. |
| 5,648,124 A | 7/1997 | Sutor |
| 5,698,271 A | 12/1997 | Liberti et al. |
| 5,866,099 A | 2/1999 | Owen et al. |
| 6,120,856 A | 9/2000 | Liberti et al. |
| 6,204,033 B1 | 3/2001 | Muller-Schulte |
| 6,461,874 B1 | 10/2002 | Ni et al. |
| 7,169,618 B2 | 1/2007 | Skold |
| 7,989,065 B2 | 8/2011 | Winstead et al. |
| 8,835,186 B2 | 9/2014 | Jablonski et al. |
| 2002/0000398 A1 | 1/2002 | Skold |
| 2002/0090638 A1 | 7/2002 | Ni et al. |
| 2003/0104359 A1 | 6/2003 | Cuthbertson et al. |
| 2003/0135038 A1 | 7/2003 | Kleiber et al. |
| 2004/0151704 A1 | 8/2004 | Berenson |
| 2007/0026435 A1 | 2/2007 | Templer |
| 2007/0036722 A1 | 2/2007 | Rongved et al. |
| 2009/0176201 A1 | 7/2009 | Jablonski et al. |
| 2010/0012880 A1 | 1/2010 | Rampersaud et al. |

(Continued)

FOREIGN PATENT DOCUMENTS

| | | |
|---|---|---|
| CN | 102617810 B | 9/2014 |
| JP | 2014-156411 | 8/2014 |
| WO | WO 1998/051435 | 11/1998 |
| WO | WO 2009/047587 | 4/2009 |

(Continued)

OTHER PUBLICATIONS

Jana et al. Synthesis of water-soluble and functionalized nanoparticles by silica coating. Chem. Mater. 2007, vol. 19, pp. 5074-5082. (Year: 2007).*
Li et al. Carboxymethylated dextran-coated magnetic iron oxide nanoparticles for regererable bioseparation. J. Nanoscience and Nanotechnology. 2011, vol. 11, pp. 10187-10192. (Year: 2011).*
Qiang et al. Iron/iron oxide core-shell nanoclusters for biomedical applications. J. Nanoparticle Research. 2006, vol. 8, pp. 489-496. (Year: 2006).*
Wang et al. Surface engineered antifouling optomagnetic SPIONs for bimodal targeted imaging of pancreatic cancer cells. International Journal of Nanomedicine, 2014, vol. 9, pp. 1601-1615. (Year: 2014).*

(Continued)

*Primary Examiner* — Shafiqul Haq
(74) *Attorney, Agent, or Firm* — Grant IP, Inc.

(57) ABSTRACT

Processes and compositions are described for preparing new, colloidally stable, coated nanomagnetic particles useful for both in-vitro and in-vivo biomedical applications, including cell targeting and capturing cells, microorganisms, and cellular organelles or entities such as exosomes. These nanomagnetic particles can also be used as imaging contrast agents due to their small size and high magnetic moment. The nanomagnetic particles include a series of sequentially added, stabilizing surface coatings rendered onto nano-sized magnetic crystal clusters (e.g., magnetite particles) to impart colloidal stability in complex biological samples with minimal leaching of the coating materials, high binding capacity, and low non-specific binding. Another benefit of this invention is the ability to utilize both external and internal magnetic field-generating separation devices to effect separation of the magnetic nanoparticles.

18 Claims, 11 Drawing Sheets

(56) References Cited

U.S. PATENT DOCUMENTS

| | | |
|---|---|---|
| 2011/0092378 A1 | 4/2011 | Clarke et al. |
| 2011/0236884 A1 | 9/2011 | Jablonski et al. |
| 2014/0170652 A1 | 6/2014 | Sitdikov et al. |
| 2015/0051102 A1 | 2/2015 | Fu et al. |
| 2015/0219636 A1 | 8/2015 | Rychak et al. |
| 2016/0167061 A1 | 6/2016 | McNaughton et al. |
| 2019/0119641 A1 | 4/2019 | Gohel et al. |
| 2019/0127697 A1 | 5/2019 | Gohel et al. |

FOREIGN PATENT DOCUMENTS

| | | |
|---|---|---|
| WO | WO 2011/053435 | 5/2011 |
| WO | WO 2016/179053 | 11/2016 |
| WO | WO 2017/190117 | 11/2017 |

OTHER PUBLICATIONS

Dim et al., Novel targeted siRNA-loaded hybrid nanoparticles: preparation, characterization and in vitro evaluation, J. Nanobiotechnol., 2015, Article No. 61, vol. 13, No. 1 (13 pages), BioMed Central, London, UK.

Herrera et al., Synthesis and functionalization of magnetite nanoparticles with aminopropylsilane and carboxymethyldextran, J. Mater. Chem., 2008, 3650-3654, 18(31), The Royal Society of Chemistry, United Kingdom.

Hsu et al., Fast sorting of CD4+ T cells from whole blood using glass microbubbles, Technology (Singap World Sci). 2015, 38-44, 3(1), World Scientific Publishing Co. Pte. Ltd., Singapore.

Liou et al., Buoyancy-activated cell sorting using targeted biotinylated albumin microbubbles, PLoS One, 2015, e0125036, 10(5), Public Library of Science, San Francisco, CA, US (15 pages).

Massart, Preparation of aqueous magnetic liquids in alkaline and acidic media, IEEE Trans. Magn., 1981, 1247-1248, 17(2), Institute of Electrical and Electronics Engineers (IEEE), Piscataway, New Jersey, USA.

Miltenyi et al., High Gradient Magnetic Cell Separation With MACS, Cytometry, 1990, 231-238, 11(2), Wiley-Liss, New York, NY, US.

Minard et al., Magnetic particle detection (MPD) for in-vitro dosimetry, Biosens. Bioelectron., 2013, 88-93, 43, Elsevier Applied Science, Barking, Essex, England.

Schwertmann et al., Ferrihydrite, Iron Oxides in the Laboratory: Preparation and Characterization 2nd Edition, 2000, 103-112, Ch. 8, VCH Publication, Weinheim, New York, NY, US.

Shi et al., Binding and isolation of tumor cells in biological media with perfluorocarbon microbubbles, Methods, 2013, 102-107, 64(2), Academic Press, San Diego, CA, US.

Shi et al., Isolation of rare tumor cells from blood cells with buoyant immunomicrobubbles, PLoS One, 2013, e58017, 8(3), Public Library of Science, San Francisco, CA, US (9 pages).

Wetzel et al., Temperature Behaviour of Human Serum Albumin, Eur. J. Biochem., 1980, 469-478, 104, Springer, Berlin, New York.

Makridis et al., "A facile microwave synthetic route for ferrite nanoparticles with direct impact in magnetic particle hyperthermia" Mater Sci Eng C Mater Biol Appl. (2016) 63:663-670.

International Search Report and Written Opinion dated Sep. 15, 2016 in International Patent Application No. PCT/US2016/030327, filed on Apr. 30, 2016 and published as WO 2016/179053 on Nov. 10, 2016.

International Preliminary Report on Patentability dated Nov. 7, 2017 in International Patent Application No. PCT/US2016/030327, filed on Apr. 30, 2016 and published as WO 2016/179053 on Nov. 10, 2016.

Extended European Search Report dated Oct. 10, 2018 in European Patent Application No. 16789869.1, filed on Apr. 30, 2016 and published as EP 3 288 912 on Mar. 7, 2018.

Pan et al., "Antibody-functionalized magnetic nanoparticles for the detection of carcinoembryonic antigen using a flow-injection electrochemical device" Anal BioAnal Chem (2007) 388:279-286.

Sun et al., "Magnetic nanoparticles in MR imaging and drug delivery" Advanced Drug Delivery Reviews (2008) 60(11):1252-1265.

International Search Report dated Sep. 28, 2017 in International Patent Application No. PCT/US2017/030317, filed on Apr. 30, 2017 and published as WO 2017/190117 on Nov. 2, 2017.

International Preliminary Report on Patentability dated Nov. 15, 2018 in International Patent Application No. PCT/US2017/030317, filed on Apr. 30, 2017 and published as WO 2017/190117 on Nov. 2, 2017.

Plouffe et al.,"Fundamentals and Application of Magnetic Particles in Cell Isolation and Enrichment" Rep Prog Phys. (2015) 78:1-76.

Office action dated Aug. 16, 2019 in U.S. Appl. No. 15/582,717, filed Apr. 30, 2017 and published as U.S. 2019-0127697 dated May 2, 2019.

Supplementary European Search Report dated Oct. 24, 2019 for EP Patent Application No. 17790625.2, filed Apr. 30, 2017 and published as EP 3 448 981 dated Mar. 6, 2019.

Lee et al., "Enhancing immunoassay detection of antigens with multimeric protein Gs" Biosensors and Bioelectronics (2011) 28:146-151.

* cited by examiner

CD4+ lymphocyte

CD4- lymphocyte

CD14+ monocyte anti-CD14 antibody conjugated microbubble anti-CD4 antibody conjugate nanomagnetic particle

STABLE NANOMAGNETIC PARTICLE DISPERSIONS

RELATED APPLICATION

This application claims the benefit of and priority to U.S. provisional patent application Ser. No. 62/156,141, filed 1 May 2015 and having the same title, the contents of which are hereby incorporated by reference in their entirety for any and all purposes.

BACKGROUND OF THE INVENTION

Magnetic particle-based technologies for the separation and isolation of cells, nucleic acids, proteins, and other biomolecules have become established and improved over the past several decades. Magnetic particles are typically conjugated with specific targeting moieties such as antibodies or nucleic acids, allowing the particles to bind to the target molecules found in complex mixtures such as cell populations or protein and nucleic acid mixtures. The magnetic particles bound to the target biological material can then be separated from the mixture using magnetic field devices, providing a purification or enrichment method for the target. Such magnetic particle-based biological target isolation approaches have been used to isolate or enrich eukaryotic cells bearing target antigens, bacterial species, nucleic acids, and proteins. They have also been used in clinical testing applications such as serving as solid supports for immunoassays or radioimmunoassays (RIA).

Methods for preparing magnetic particles for such applications are typically of two general types. One general method involves dispersing the magnetic particles evenly within a polymeric matrix during preparation of the polymeric particles, constructing a magnetic material shell around a polymeric particle core, or introducing magnetic material into pre-existing pores within the polymer particles. Examples of the former method can be found, for example, in U.S. Pat. No. 4,358,388, and of the second method in U.S. Pat. Nos. 5,320,944 and 5,091,206. The latter method is exemplified in U.S. Pat. Nos. 5,648,124 and 4,654,267. All of these methods result in magnetic particles of greater than 0.3 um (micrometer) in size.

The second general method for preparing magnetic particles for biomaterial applications involves creating bare magnetic material particles first that serve as the core of a larger particle created by constructing a shell around the first magnetic material core. One form of primary coating has been a silane coat, but other coatings have also been described. For example, U.S. Pat. No. 3,933,997 describes the use of a silane coupling agent that coats magnetic particles and directly conjugates to specific antibodies. This material was reportedly intended for use in RIA methods. U.S. Pat. No. 4,554,088 describes construction of a metal or iron oxide particle core that is coated by a polymeric silane to which bioaffinity molecules such as antibodies are directly coupled. U.S. Pat. No. 4,695,392, a division of the aforementioned '088 patent, further defines the silane coat to which bioaffinity molecules are directly attached as having two discrete functionalities—the first to adsorptively or covalently couple to the metal oxide core particle and the second to covalently couple to bioaffinity organic molecules. In both patents the size of particles is defined as ranging from 0.1 um to 1.5 um. U.S. patent application publication no. 2007/0026435, now abandoned, discloses a hydroxysilane, preferably hydroxyalkyltrialkoxysilane, primary coating on a magnetic particle core. In this application the particle sizes ranged from 0.1 um to 100 um, and the particles were specified for use in isolation of specific nucleic acids from mixtures. The magnetic particles disclosed in both the '392 patent and the 2007/0026435 publication produce highly aggregated magnetic particles upwards of 1 um in diameter when strictly adhering to the cited examples contained therein. U.S. Pat. No. 7,169,618 discloses preparation of magnetic particles of a size range from 0.07 um to 0.45 um that are first coated with an organosilane that is then conjugated with a polysaccharide material via a pendant functional group on the organosilane. U.S. patent application publication no. 2010/0012880 discloses a magnetic particle having a magnetic material core with a primary hydrophobic protective layer over which is layered a hydrophilic alkylsilane coating. Such particles are disclosed as being from 0.2 um to 0.4 um in diameter.

Distinct from silane coatings that also serve as the coupling reagent to bioaffinity molecules, non-silane primary coatings on core magnetic particles have also been reported. These include polyglutaraldehyde (see, e.g., U.S. Pat. No. 4,267,234), acrylamide, n-butylacrylate, or N,N'-methylenebisacrylamide (see, e.g., U.S. Pat. No. 4,454,234), polyacrolein (see, e.g., U.S. Pat. No. 4,783,336), polyvinyl alcohol (see, e.g., U.S. Pat. No. 6,204,033), natural polymers like dextran (see, e.g., U.S. Pat. No. 4,452,773), and bovine serum albumin (see, e.g., U.S. Pat. No. 4,795,698). All of these magnetic particle primary coatings reportedly serve as substrates to which additional biomolecules such as antibodies or nucleic acids may be conjugated. With all of these methods, the shapes and sizes of the resultant bioaffinity magnetic particle products are not easily controlled, the size range of the particle products are relatively broad, the diameters are typically greater than 0.5 um, and the product particles tend to easily adhere to one another forming particle clumps.

Despite these advances, the need exists for further improved magnetic particles, as well as processes for making and using such particles.

SUMMARY OF THE INVENTION

This invention addresses these needs, and provides a highly reproducible process for producing silane-(glass) encapsulated nanomagnetic particles onto which is further encapsulated a stabilizing protein/polymer composite mixture to result in resuspendable nanomagnetic particles that can withstand multiple rounds of exposure to strong magnetic fields (e.g., 0.5-1.0 Tesla) without any substantial increase in particle size. Such multi-layered nanomagnetic particles are then made specific for one or more desired biomolecule species, cell, or tissue type by covalently attaching targeting moieties to the protein/polymer composite layer. The resultant nanomagnetic particles additionally have a very narrow size distribution with a polydispersity index (PDI) value 0.10) approaching that of monodisperse particles. Nanomagnetic particles of diameters from about 5 nm to about 500 nm can be produced using this invention, preferably from about 30 nm to about 300 nm. Preferred nanoparticles of the invention include a magnetic core particle comprised of a ferrous oxide, particularly magnetite ($Fe_3O_4$) crystal clusters. Other preferred magnetic cores comprise $Fe_2O_3$; a chromium oxide, for example, $CrO_3$; or a stable metal oxide that comprises a substituted metal ion, e.g., Mn, Co, Ni, Zn, Gd, and Dy. Particularly preferred magnetic core particles, including those comprised of magnetite crystal clusters, have diameters ranging from about 5 nm to about 300 nm.

The nanomagnetic particles so produced have three layers of coatings around the core nano-sized magnetic particles, namely a silane or glass layer, a protein/polymer layer, and finally an outermost layer that is comprised of targeting moieties, which are one member of a bioaffinity ligand pair, such as an antibody for targeting an antigen of interest, a cell surface receptor or receptor fragment, etc. The targeting moiety or bioaffinity ligand (which may be, for example, an antibody or antigen-binding antibody fragment, streptavidin, peptide, nucleic acid polymer, or other receptor or ligand of interest) is preferably covalently conjugated to the ample functional groups present on the protein/polymer layer. In preferred embodiments, the glass layer is a silane layer formed from organofunctional alkoxysilane molecules, optionally organofunctional alkoxysilane molecules that comprise a couplable end group, optionally a couplable end group selected from the group consisting of an amino, sulphydryl, carboxyl, and hydroxyl end or reactive group. The end group may be protected or unprotected; if protected, a deprotection step is preferably used prior to coupling of the protein/polymer composite layer. In preferred embodiments, the protein/polymer composite layer is covalently bound to the glass layer. Preferably, the protein/polymer composite layer is comprised of serum albumin, e.g., bovine or human serum albumin, dextran, or casein. In some embodiments, the protein/polymer composite layer is permanently bound by heating the composition from about 45° C. to about 85° C. The targeting moiety or bioaffinity ligand (i.e., one member of a high affinity binding pair) is then conjugated, preferably covalently, to the protein/polymer layer. Preferred targeting moieties include antibodies (preferably monoclonal antibodies), antigen-binding antibody fragments (e.g., Fab fragments), cell surface receptors, ligand-binding extracellular domains of cell surface receptors, nucleic acids (including nucleic acid-based aptamers), avidin, streptavidin, biotin, and pharmaceutical compounds for purposes of targeted drug delivery.

The targeted nanomagnetic particles of the invention behave as stable colloids when combined in a reaction mixture with complex liquids, for example, mammalian whole blood or a fraction of mammalian whole blood. Moreover, targeted nanomagnetic particles of the invention preferably exhibit no significant or deleterious change in magnetic, bioaffinity, and/or particle size and targeting properties during storage over long periods, e.g., 1 year to 5 years. Preferred sources of biological samples are those obtained from mammals, including humans, as well as from companion animals (e.g., cats and dogs) or those of commercial significance (e.g., cattle; fowl such as chickens, turkeys, and ducks; goats; horses, pigs, sheep, etc.).

Compositions comprising the nanomagnetic particles of the invention can be formulated in any suitable manner, including dry, readily dispersible formulations (e.g., lyophilized formulations) or liquid compositions. After preparation, such compositions are typically dispensed in desired quantities (e.g., in an amount suitable for performing a single magnetic separation, or alternatively, multiple separations) into suitable containers that are then often packaged into kits for subsequent distribution and use. Kits according to the invention preferably include instructions for use of the reagents in the kit, including use of nanomagnetic particles of the invention to perform one or more desired magnetic separations. In some embodiments, such kits may include a plurality of targeted nanomagnetic particle species, wherein each targeted nanomagnetic particle species comprises a different targeting moiety species. Preferably, in kits that contain a plurality of different targeted nanomagnetic particle species, each species is preferably packaged in a separate container in the kit. In some embodiments, such kits may also include compositions for also performing buoyant separations of one or more particular biomolecule species from a reaction mixture prepared from a biological sample.

Thus, this invention relates to the use of magnetic separation to separate target biomolecules, for example, cells, organelles, exosomes, oncosomes and other biological materials to be isolated or separated from complex mixtures such as biological samples. To accomplish such separations, this invention provides a new class of patentable nanomagnetic particle compositions for use in magnetic separation procedures.

These and other aspects, objects, and embodiments of the present invention, which are not limited to or by the information in this Summary, are provided below, including in the claims.

DETAILED DESCRIPTION

Figure 1:
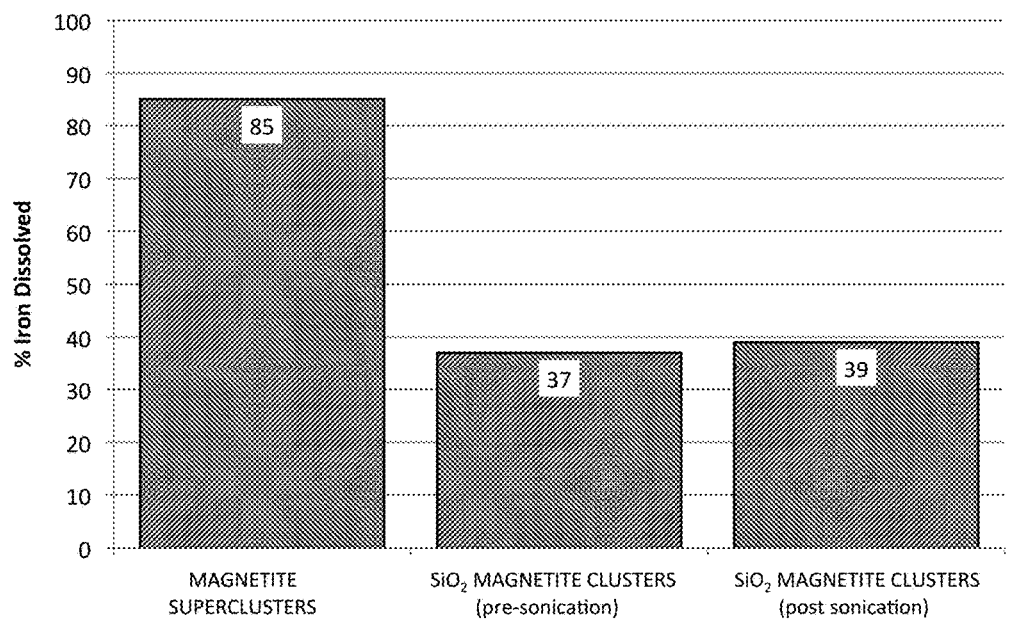
FIG. 1 shows the results of an acid dissolution study performed on non-silanized silanized and silanized nanomagnetic particles of the invention pre- and post-sonication. The plot shows the percentage of iron dissolved after a 15 min. exposure to 4 M HCl.

As those in the art will appreciate, the following detailed description describes certain preferred embodiments of the invention in detail, and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only, and is not intended to limit the scope of the invention defined by the appended claims.

Numerous methods are known for analyzing and sorting populations of cells and other biomolecules, including methods based on cell size, density, or granularity in which separation is achieved by sedimentation, alone or in combination with density gradients and centrifugation or elution. Other methods include those based on differential resistance of cells to osmotic lysis, as can be used, for example, to separate white blood cells from whole blood. Furthermore, methods of depleting (i.e., reducing the number of) unwanted cells (or other biomolecules) from a more complex biological sample using specific antibodies that react with a cell surface marker can be used to remove or reduce the numbers of cells expressing that marker. Still other cell separation methods include flow cytometry and magnetic cell sorting (e.g., using magnetic particle-conjugated antibodies), as well as other methods that employ antibody affinity (or other high affinity binding pairs) to particular biomolecules, including cell surface proteins. Using these technologies, positive enrichment or depletion of particularly desired, i.e., "targeted" or "target", cell populations (i.e., those expressing a marker that can be targeted by the high affinity binding moiety (e.g., an antibody, Fab fragment, receptor, etc.) conjugated to the labeled detection/separation reagent can be achieved.

Thus, this invention addresses the separation of one or more desired or target biomolecule species, particularly one or more target cell populations, from a more complex biological sample such as a cellular mixture (e.g., whole blood, a homogenized biopsy or tissue sample, etc.). A "target biological material" or "target biomolecule" refers to any biological substrate, for example, cells, organelles, and other biological materials, a user desires to isolate, enrich for, deplete, or target and for which a specific binding moiety (partner) can be prepared so as to specifically label or bind the material. The list of suitable target biomolecules is extensive, and includes microorganisms such as protozoa, bacteria, yeast, and other fungi, cultured cells from multi-celled organisms (including mammalian and other vertebrate cells, viruses, and fragments of the cells and viruses), eukaryotic cell populations that express one or more targetable cell surface antigens, and organelles or other subcellular structures (e.g., exosomes, proteasomes, ribosomes, etc.) that include a targetable protein or other biomolecule (e.g., a carbohydrate, lipid, etc.). Indeed, any biological material (i.e., biomolecule), either a single molecule (e.g., a protein) or an organized or amorphous aggregate of one or more molecules (of the same of different molecular species), that can be targeted by a targeting moiety can be isolated or purified using the nanomagnetic particles and methods of the invention.

The instant methods are based on the use of the new patentable class of targeted nanomagnetic particles described herein, which can be used to separate targeted biomolecules (up to and including intact, viable cells) from other components in a reaction mixture by magnetic cell separation techniques. If desired, other separations can also be performed in order to enrich or deplete one or more other biomolecule species (e.g., cell populations) present in the reaction mixture (as a result of being present in the original sample to be analyzed). Indeed, in a related aspect, targeted biomolecular separation based on the use of targeted buoyant microparticles (e.g., microbubbles and the like) can be used in conjunction with magnetic separation for parallel or serial processing of a biological sample in order to enrich for two or more desired cell populations (or other biomolecule species) or to enrich for at least one target cell population (or other biomolecule species) and deplete another. Particularly preferred proteins that can be targeted, for example, by a monoclonal antibody specifically reactive therewith, to separate target cell populations from biological samples include the following cell surface proteins:

| Human Specificity | Mouse Specificity |
| --- | --- |
| CD4 | CD4 |
| CD8 | CD8 |
| CD19 | CD19 |
| CD14 | CD11c |
| CD56 | CD25 |
| CD25 | Ter119 |
| CD235 | CX3CR1 |
| Epcam/CD326 | CD20 |
| TSPAN33 | |
| CD20 | |
| Lfr5 | |
| ERBB2/HER2 | |
| GPR35/CXCR8 | |

In the context of the invention, targeted separation (for enrichment or depletion) is achieved through the use of a targeting moiety conjugated to the separable particle (e.g., a nanomagnetic particle of the invention, a conventional magnetic particle, a buoyant particle (e.g., a microbubble), etc.). The targeting moiety is typically a high affinity binding reagent that can conjugated to the separable particle by a suitable chemistry (preferably one involving covalent bonding that does not disrupt binding between the high affinity binding reagent and the targeted biomolecule, preferably a protein expressed on the surface of a targeted cell population, organelle, or other biomolecule). Examples of such high affinity binding reagents include members of high affinity binding pairs. Such members include antibodies (particularly monoclonal antibodies), antigen-binding antibody fragments (e.g., Fab fragments), or another member of a high affinity bending pair (one of which is conjugated to the separable particle and the other of which is the "target" present on the biomolecule or structure being targeted). In some embodiments, the high affinity binding reagent and/or separable particle to which it is conjugated is labeled with a detectable agent suitable for cell separation (e.g., FACS), such as a fluorescent dye.

High affinity binding reagents conjugated to separable (e.g., by magnetic or electric fields, buoyancy, etc.) particles can be used to separate desired biomolecules (e.g., a cell population expressing a particular cell surface antigen) from other reaction mixture components under conditions that allow the binding reagents to specifically bind their corresponding targets (e.g., antigens in the case of antibodies, antigen-binding antibody fragments, etc.).

The practice of the separation methods of the invention comprise the following steps: in a reaction mixture, immobilizing the target biomolecule, for example, a target cell population expressing a particular cell surface marker, present in a biological sample known or suspected to contain the target biomolecule, which biomolecule is specifically bound by the targeting moiety of a nanomagnetic particle of the invention in a ferromagnetic matrix through the use of a magnetic field; washing the matrix to remove unbound components in the reaction mixture; and removing the magnetic field to elute the targeted biomolecule from the matrix. As a result, a target biomolecule (e.g., a target cell population) is enriched; in addition or alternatively, the biological sample is depleted of the target biomolecule (provided that at the material washed from the matrix is retained for further use). Elution of material from the ferromagnetic matrix can be performed using gravity flow, centrifugation, vacuum filtration, or a pressure gradient.

The term "magnetic separation" refers to separation procedures for constituent components of complex samples, e.g., biological samples. Such procedures include magnetic separation mediated by targeting moieties that comprise one member of a high affinity binding pair (e.g., a monoclonal antibody that specifically binds a target cell surface antigen) conjugated or otherwise linked to a nanomagnetic particle according to the invention. Magnetic separation can be combined with other separation procedures, including those that employ targeted buoyant particles and/or separation techniques known in the art that also rely on high affinity binding pairs (e.g., antibodies and their cognate antigens), for instance, affinity chromatography, "panning" (where one member of the high affinity binding pair is attached to a solid matrix (e.g., the well of a microtiter plate). Fluorescence activated cell sorting (FACS) can also be used if fluorescent tags are included in the targeted separable particles. Indeed, any now known or later developed ligand-dependent separation technique can be used in conjunction with positive and/or negative separation techniques that rely on physical properties of the target biomolecule rather than affinity, including filtration, size exclusion chromatography, and density gradient centrifugation.

The invention also includes kits for performing the magnetic separation methods described herein, alone or in addition to other separation methods. Such kits include targeted nanomagnetic particles of the invention that target a desired biomolecule, for example, a cell surface antigen expressed on the surface of a particular cell type. The targeted nanomagnetic particles are typically packaged in containers that include such quantities of the particles as are needed to perform one or more magnetic separation procedures. Instructions (or a link or website address containing such instructions) for use of the targeted nanomagnetic particles (and any other included reagent(s), e.g., targeted buoyant microbubbles) are also typically included in any such kit.

Magnetic Separation

Among techniques known for separating components of a biological material or sample are those that make use of magnetic separation techniques. Magnetic separation methods typically selectively retain magnetic materials in a chamber or column disposed in a magnetic field. Such methods typically include passing a biological material or sample through one or more separation columns. Briefly, the biological material or sample is magnetically labeled by attachment to targeted nanomagnetic particles of the invention through the use of a targeting moiety conjugated to the particles, which targeting moiety targets a desired (or "target") biomolecule known or suspected to be present in the sample, for example, displayed on the surface of certain cells known or suspected to be present in the same. A suspension of the labeled target sample is then applied to the separation chamber or column. To separate the targeted biomolecule species from the remainder of the reaction mixture, the targeted biological material is retained in the chamber in the presence of a magnetic field. The retained targeted biological material can then be eluted by changing the strength of, or by eliminating, the magnetic field.

In some embodiments, high gradient magnetic separation (HGMS) is used (Miltenyi et al., Cytometry, 11, 231 (1990)). In HGMS, a matrix of material of suitable magnetic susceptibility such as iron wool or steel beads is placed in a chamber or column such that when a magnetic field is applied, a high magnetic field gradient is locally induced close to the surface of the matrix, permitting retention of complexes of the magnetized particles and targeted biological material formed through the association of the members of the high affinity binding pairs present in the mixture.

The targeted nanomagnetic particles and methods of the invention can be used for the magnetic separation of, or to magnetically label and, if desired, isolate, any desired target substance or analyte (e.g., cells, organelles, etc.). Of particular interest is separating a specific biomolecule from a complex biological mixture. The present invention has great utility, in that almost any target substance may be separated once a specific binding member for that substance is available. The targeting moiety can be any member of a specific, high-affinity binding pair, or a substance associated with a member of a specific, high-affinity binding pair. For example, a cell surface antigen-antibody binding pair can be used to isolate the antigen itself, cells that express the antigen, a particular organelle involved in processing of the antigen, etc. The devices and methods of the present invention are also advantageously applied to diagnostic techniques involving the binding of a receptor and ligand, such as immunoassays, and the like.

Targeted Nanomagnetic Particles

Two classes of magnetic oxides, ferrites and non-ferrites, can be used for the production of the targeted nanomagnetic particles of the invention. Ferrites, or iron-containing transition metal oxides, can generally be represented as $XO.Fe_2O_3$, where "X" may be Fe, Ni, Cr, Co, Mn, Mg, Mo, Gd, Cu, V, Dy, Ey, Tm, or Yb. Therefore, in the process of synthesizing magnetite superclusters, one would substitute the $Fe^{2+}$-containing iron salt with one of the aforementioned divalent metal ion salts. The most preferable in this class of ferrites is $FeO.Fe_2O_3$, which is better known as magnetite or $Fe_3O_4$. The non-ferrite class of magnetic oxides are void of the iron atom but instead are substituted with a combination of two or more ions of these transition metals: Cr; Co; Mn; Ni; Mo; Gd; Dy; Ey; Tm; and Yb. Such non-ferrite-based magnetic oxides typically produce a spectrum of colored nanomagnetic particles but are less magnetically responsive than the ferrite class of magnetic oxides.

Magnetite crystals were first synthesized almost a century ago. The subsequent processing and stabilization of the magnetite crystals has spawned many different types of magnetic particles of different sizes, with different surface coatings, and for different applications. In preferred embodiments, magnetite ($Fe_3O_4$) crystals are first synthesized using any suitable process, including the well-known aqueous based co-precipitation method [Massart 1982, Schwertmann 1991]. Stoichiometric mixtures of ferrous ($Fe^{2+}$) and ferric ($Fe^{3+}$) iron salts are titrated with a strong base under an inert atmosphere to yield 1 um-3 μm diameter magnetite crystals. Variables such as the mole-ratio of the iron salts (e.g., 1.0 M $Fe^{2+}$: 2.0 $MFe^{3+}$ to 2.0 M $Fe^{2+}$: 1.0 $MFe^{3+}$), reaction temperature (e.g., 40° C. to 95° C.), type of base counterions (e.g., ammonium, sodium, potassium) used, and the rate of base addition (e.g., 2 mL/minute to 200 mL/minute) are optimized in order to produce the highest quality 'bare' magnetite crystals. These magnetite crystals are next sonicated at high power in order to yield quasi-stable 90 nm-110 nm (nanometer) sized nanomagnetic particles that are immediately silanized using an aqueous acidic silanization procedure concomitant with high temperature dehydration in order to obtain silanized nanomagnetic particles.

Silanization can be accomplished using any suitable process. For example, after 25 minutes of sonication at high power (750 W) using a 0.5 inch titanium probe tip, nanomagnetic particles are transferred into a 3-neck round-bottom glass reaction vessel kept under nitrogen gas containing 50 v % glycerol together with an overhead stirrer. A 10 wt % (relative to the iron mass) solution of sodium silicate is then added at 0.5 ml/minute, followed immediately by the addition of 0.5 M glacial acetic acid at 1 mL/minute until a pH of 6 is attained. The temperature is then raised to 180° C. and the mixture is allowed to dehydrate for at least 2 hours, then cooled and washed using water.

In various preferred embodiments, the 'bare' magnetite crystals are first peptized using a strong metal ion chelating agent such as EGTA in order to make available additional seed hydroxyl groups for condensation with the silanization reagent. Peptization is achieved by sonicating the 2 um size magnetite superclusters in the presence of the chelating agent (e.g., EGTA) in order to introduce additional hydroxyl groups onto the magnetite particles and afford greater colloidal stability. In yet another preferred embodiment, two silanization reagents are used sequentially in order to both enhance encapsulation as well as to provide additional couplable groups by virtue of the inherent functionalities present in the secondary silanization reagent. Sequential silanization can be achieved, for example, by first silanizing sonicated magnetite particles using sodium silicate as described above, followed immediately by the addition of an amino-silane such as aminopropyl-trimethoxysilane (APTS) prior to dehydration at 180° C. (see Example 2, below).

A second round of high power sonication, albeit brief, is performed in order to reduce the particle size, preferentially to 95 nm-105 nm. Next, these silanized nanomagnetic particles are mixed with a heated solution containing a protein/polymer mixture, for example, BSA (bovine serum albumin) and the polysaccharide dextran (99 wt % BSA:1 wt % dextran to 50 wt % BSA:50 wt % Dextran). This can be accomplished, for example, by heating a solution containing a mixture of BSA and Dextran to 70° C. just prior to mixing it with sonicated magnetite particles in a sealed 3-neck reaction vessel under a nitrogen atmosphere. The coating process is allowed to proceed for 30 minutes. The suspension then is cooled and washed using, for example, a high-field magnetic dipole separator.

Heating concentrated BSA solutions to temperatures in excess of 58° C. is known to produce irreversible aggregates of BSA mediated by the formation of disulphide bonds and hydrogen bonding of beta sheets between individual BSA molecules [Wetzel, 1980]. In one preferred embodiment, maleimide groups are introduced into the BSA protein prior to mixing with the sonicated silanized particles in order to further promote the formation of disulphide bonds. The BSA/Dextran coated nanomagnetic particles are then washed with the aid of strong dipole/quadrupole-type magnetic separators to remove excess coating materials as well as to narrow the size distribution of the particles to a final size of about 110 nm. The initial wash supernatant from this magnetic fractionation step contains a significant amount (~50% by iron mass) of 30 nm-80 nm size BSA/Dextran coated nanomagnetic particles. Such smaller sized nanomagnetic particles can also be effectively utilized for magnetically capturing/purifying intracellular and/or extracellular targets such as, but not limited to, endosomes and exosomes, respectively. The BSA/Dextran coated nanomagnetic particles so produced typically have a PDI of ≤0.1. This PDI number is a measure of the width of the particle size distribution and is obtained automatically during DLS based size measurements. Generally, polydispersity indices less than 0.1 are typically referred to as "monodisperse" particle suspensions. More precisely, PDI=the square of the standard deviation divided by the mean diameter and is a dimensionless number. Bioaffinity ligands, i.e., "targeting moieties", such as antibodies and/or streptavidin, are then conjugated to the 110 nm diameter BSA/Dextran coated nanomagnetic particles using standard hetero/homo-bifunctional coupling chemistries. Streptavidin-coated nanomagnetic particles so prepared are further heat-treated with a high ionic strength salt solution (1 M to 5 M NaCl) in order to stabilize the surface coatings on the particles.

In some embodiments, the targeting moieties associated with a targeted nanomagnetic particle of the invention are labeled with a detectable label, for example, a radioisotope or fluorescent molecule, in order to render the particles, or the particle/targeted cell (or other biomolecular structure) complexes detectable through the use of a complementary label detection instrument or system. Such labels can be included in the magnetic core particle and/or in one or more of the outer layers of a nanomagnetic particle of the invention. In other embodiments where particle/cell detection is desired, a technology for detecting the particle's magnetic signal may be employed, a representative example of which is SQUID technology, which can be used to detect magnetic labels by virtue of the magnetic fields that they produce [Clarke and Braginski, SQUID Handbook, vol 1, (2004)].

In Vivo Applications

The targeted nanomagnetic particles of the invention can be adapted for many in vivo diagnostic and therapeutic uses, including imaging, cell therapies, and delivery of therapeutic agents to cells.

Cell Therapy

Today, many human diseases cannot be satisfactorily treated with standard pharmaceuticals. For some of these diseases, cell therapies offer an attractive alternative. Cell-based therapies generally require significant handling and processing of cellular products. Current cell therapy methods require substantial infrastructure and equipment to meet manufacturing and regulatory requirements, including good manufacturing practices, which involve the use of suitable clean rooms and personnel to maintain rooms, devices, production, quality control, and quality assurance procedures under conditions that ensure non-contamination of samples to maintain sterility. Cell-based products are typically processed using a combination of different devices and disposables. Transfer of products and reagents in such processes can be manual and/or automated.

Magnetic cell separation can include both enrichment and depletion procedures. If target cells can be identified using cell surface proteins (or other cell surface biomolecules), they can be enriched to high purity through one or more rounds of enrichment and/or depletion. In other cases, target cells can be identified and removed from the resulting cellular product, which may be a heterogeneous mixture of different desired cells in which the number of cells targeted for removal has been reduced. Of course, combinations of both enrichment and depletion can be used.

Magnetic labeling of cells using targeted nanomagnetic particles of the invention includes a suitable targeting moiety, typically a specific binding member of a high affinity binding pair. The target cell/particle complexes can then be isolated using a magnetic separation device. The isolation of multipotent cells, e.g., hematopoietic stem or progenitor cells, is of particular interest, although the present invention can applied to a wide range of cell types or other biological materials or samples.

Cellular products produced in accordance with the invention can be used in therapy immediately or stored for later use using known methods. Formulation steps include adjusting the separated cell-containing preparation to a desired volume or cell concentration, exchanging processing liquids with injectable solutions, adding stabilizers (e.g., autologous plasma or serum, serum albumins, other proteins or synthetic polymers, etc.) or adjuvants, supplementation with cryoprotective agents such as DMSO for subsequent storage, drawing of retention aliquots for quality control, delivery to combinations of bags or syringes for infusion, etc.

Importantly, the targeted nanomagnetic particles of this invention can be sterilized using any suitable method, including filter sterilized (due to the particles' small size) for use in therapeutic and/or in-vivo/in-vitro procedures where sterile processing is mandated or desired.

In Vitro Applications

The targeted nanomagnetic particles of the invention can also be adapted for many in vitro diagnostic and therapeutic uses. Magnetic particles have been used in the past to isolate or enrich eukaryotic cells, bacterial species, nucleic acids, and proteins. Beside particle isolation or cell separation, magnetic nanoparticles have also been used to stimulate or activate cells by coating cell activating ligands on the particle surface so that full three dimensional aspects of target engagement, often important in biological systems, are more accurately reproduced as compared to solution phase activation protocols. In recent years, magnetic particles have been studied for use in newer in-vitro tests. Examples of these include evaluation of the potential health effects of nanomagnetic particles (Kevin et al, Biosensors and Bioelectronics, 43, 88 (2013)) and of nanotechnology-based systems for delivery of si-RNA (Dim, et al, J. Nanobiotechnology, 13, 61 (2015)). Nanoparticles are also in research and development testing for application as targeted heating components that can develop localized magnetic hyperthermia conditions for the treatment of cancer (Makridis, et al., Mater Sci Eng C Mater Biol Appl., 63, 663 (2016).

EXAMPLES

The following Examples are provided to illustrate certain aspects of the present invention and to aid those of skill in the art in its practice. These Examples are in no way to be considered to limit the scope of the invention in any manner, and those having ordinary or greater skill in the applicable arts will readily appreciate that the specification thoroughly describes the invention and can be readily applied to carry out the objects and obtain the ends and advantages mentioned, as well as those inherent therein.

1. Synthesis of Silanized BSA/Dextran-Coated Nanomagnetic Particles

This example describes a preferred method for synthesizing silanized BSA/Dextran coated nanomagnetic particles for use in the invention. This synthesis is carried out in three stages and involves first, the synthesis of the bare (uncoated) magnetite superclusters followed by the silanization of these superclusters, and, finally, a protein/polymer coating step using a mixture of BSA/Dextran.

Briefly, 5.02 g of ferrous sulfate and 7.22 g of ferric sulfate (SIGMA-ALDRICH; St. Louis, Mo.) are separately dissolved in 25 mL of degassed deionized water and then added into a reaction vessel containing 250 mL of degassed deionized water at 70° C. with continuous stirring. Next, 35 mL of 10 M ammonium hydroxide (SIGMA-ALDRICH; St. Louis, Mo.) is added into the reaction flask at a rate of 9 mL/minute, and the formation of the magnetite superclusters is allowed to proceed for 30 minutes. The precipitate is then exhaustively washed with deionized water using an in-house built ceramic low-gradient magnetic separator (LGMS) and finally stored under a nitrogen cap in degassed deionized water. These magnetite superclusters typically have a hydrodynamic diameter in the range of 2 to 3 um as measured by dynamic light scattering (Malvern Nano-S ZetaSizer; Westborough, Mass.).

Next, 1.65 g of the magnetite superclusters are sonicated in a 100 mL volume of low ionic strength phosphate buffer (ACS grade monosodium phosphate having a molecular weight of 137.99 g/mole) with the aid of the VCX750 Ultrasonic processor (Sonics & Materials Inc., Newtown, Conn.) using a cooled, jacketed reaction beaker to a final size of ~110 nm and then immediately transferred into a reaction flask contained in a silicone oil-bath. Next, 2.5 mL of a 66 mg/mL of sodium silicate ($SiO_2^-$) solution (SIGMA-ALDRICH; St. Louis, Mo.) is added into the reaction flask at a rate of 0.5 mL/minute followed by acidification with ~8 mL of 0.5M acetic acid added at 1 mL/minute to a final pH value of 6.0. The temperature of the oil-bath is then raised to 170° C. and the particle suspension is allowed to dehydrate for about 3 hours in order to promote the surface silanization of the nanomagnetic particles. After cooling to room temperature, the particle suspension is placed into a LGMS magnetic separator for 30 minutes and the magnetically pelletized particles are recovered and washed exhaustively with a low ionic strength HEPES buffer (VWR, Visalia, Calif.). These silanized or $SiO_2$-derivatized magnetite clusters typically have a hydrodynamic size of about 200 nm and dissolve much more slowly in strong acid than their non-silanized versions (see Table 1, below).

To prepare the BSA/Dextran coated nanomagnetic particles, 1.4 g of the silanized magnetite clusters are sonicated in a 135 mL volume of low ionic strength phosphate buffer with the aid of the VCX750 Ultrasonic processor (Sonics & Materials Inc.; Newtown, Conn.) using a cooled, jacketed reaction beaker to a final size of ~100 nm and then immediately transferred into a 1 L jacketed reaction flask thermostated to 70° C. that contains 400 mL of a mixture of 20 mg/mL BSA (Lampire Biologicals; Pipersville, Pa.) and 0.2 mg/mL Dextran (SIGMA-ALDRICH; St. Louis, Mo.). This coating reaction is allowed to proceed for 30 minutes at 70° C. The coated nanomagnetic particles are then cooled to room temperature and left undisturbed overnight at 4° C.

Next, the particles are slowly decanted from the vessel with the aid of a low-field ceramic magnet held at the bottom of the vessel in order to sediment away the large size (~300 nm) particle aggregates. The collected supernatant (of ~100 nm diameter) is then subjected to 7 cycles of high-field magnetic washes in low-ionic strength HEPES buffer (VWR; Visalia, Calif.). These high-field washes, in addition to removing the excess reactants, also serves to significantly narrow the particle size distribution to values of 1:1.1 PDI. The final hydrodynamic particle size is typically about 115 nm. The overall yield starting from 1.65 g of the magnetite superclusters is typically at least 50%. The first high-field magnetic wash supernatant, which typically has a hydrodynamic size of ~70 nm and which constitutes ~35% of the total particle yield, is collected as a by-product and can be used to produce smaller size (<100 nm) nanomagnetic particle products for use as an in-vivo/in-vitro tracking/capture label as well as for magnetic cell isolations in concert with HGMS columns (see EXAMPLE 3, below).

Finally, a member of a bioaffinity ligand pair such as Streptavidin, antibodies, or other desirable ligands can be covalently conjugated to the ample BSA-derived functional groups present on these BSA/Dextran coated nanomagnetic particles using standard hetero/homo-bifunctional conjugation chemistries as will be familiar to those skilled in the art.

in lieu of sodium silicate as in Example 1, above, and the dehydration step allowed to proceed for 75 minutes at 160° C.

Another silanization agent, hydroxymethyltriethoxysilane (Gelest, Morrisville, Pa.), is very hydrophilic, and has also been successfully used to produce silanized nanomagnetic particles useful in the context of the invention. In this particular case, 15 wt % of this silanizing agent (relative to the iron content) was used and the dehydration was allowed to proceed for 2 hours at 160° C.

All of the aforementioned silanized magnetic particles have been successfully coated with BSA/Dextran mixtures as described in Example 1, above. These types of silanized nanomagnetic particles, when encapsulated with BSA/Dextran mixtures, typically exhibit 50% acid dissolution after 15 minutes exposure to 4 M HCL. Briefly, to perform dissolution, 100 uL of 0.1 mg/mL (in terms of iron content) of the particle suspension was incubated with 200 uL of 6 M hydrochloric acid and aliquots of this mixture were removed at various time intervals and assayed for the presence of elemental (or dissolved) iron by complexation with potassium thiocyanate as a colorimetric endpoint readout. Table 1, below, shows the acid dissolution behavior of all of these aforementioned silanized magnetite clusters.

TABLE 1

Percent dissolution of Iron oxide as a function of acid exposure time for various silanized magnetite clusters

| Time in 4M Hydrochloric acid (minutes) | Magnetite Superclusters | Silanized magnetite clusters | APS + Silicate silanized EGTA peptized magnetite clusters | APS only silanized magnetite clusters | Hydroxymethylsilanized magnetite clusters |
|---|---|---|---|---|---|
| 5 | 43.8% | 22.8% | 21.8% | 33.1% | 28.1% |
| 10 | 72.5% | 33.7% | 38.8% | 47.1% | 49.1% |
| 15 | 90.0% | 48.4% | 55.0% | 64.9% | 68.9% |
| 30 | 100% | 77.0% | 100% | 89.5% | 100% |
| 45 | 100% | 100% | 100% | 100% | 100% |

2. Synthesis of Nanomagnetic Particles by Peptization and Other Types of Silanizing Agents Electrolytes such as the chelating agents known more popularly as EDTA, EGTA, as well as weak bases and acids are referred to as peptizing agents in instances where they help to disperse precipitates into colloidal sols. In this example, EGTA (SIGMA-ALDRICH; St. Louis, Mo.), which is a strong iron chelating agent, is added (at 0.25 moles EGTA/mole iron) immediately after the formation of the magnetite superclusters as in Example 1, above. This chelation step is allowed to proceed for 1 hour at 70° C. prior to washing up the magnetite superclusters as in Example 1, above. Unlike the ~2.5 um size of the starting magnetite superclusters, these EGTA peptized magnetite clusters typically have a hydrodynamic diameter of about 1 um, and such a size reduction is indicative of a successful dispersion of the magnetite superclusters.

In another embodiment, a sequential silanization method is used whereby EGTA peptized magnetite superclusters are sonicated and silanized as in Example 1, above, and immediately after the addition of the sodium silicate solution, an equimolar amount of the amino-functionalized silanizing agent aminopropyltrimethoxysilane or APS (SIGMA-ALDRICH; St. Louis, Mo.) is added and the particles allowed to dehydrate for 90 minutes at 160° C. after acidification to pH 6.0. Silanization has also been achieved using just APS The data in Table 1, above, show that the silanization methods described herein indeed provide protection against acid dissolution and also serve to provide highly cross-linked silane molecules on the surface of the magnetic particles. For instance, at the 15 minute time point, 90% of the (bare) magnetite superclusters were dissolved by acid compared to only 50% to 70% of the silanized magnetite clusters.

FIG. 1 shows the results of an acid dissolution study performed on a silanized nanomagnetic particle pre- and post-sonication. This study shows that the silane (glass) coating remained intact on the nanomagnetic particle surface after the second round of high power sonication as described in Example 1, above.

Nanomagnetic particles produced without a primary glass coating are typically not stable in biological fluids such as plasma and whole blood, and, furthermore, they are prone to aggregation even in solutions of low ionic strength. Such protective functionalities (e.g., stability, reduced aggregation) provided by the silanization processes described herein significantly contribute to the practical utility of the targeted nanomagnetic particles claimed in this patent in biological research efforts as compared to other magnetic nanoparticles.

3. Derivitization, Processing and Cell Labeling Efficacy of the 70 nm BSA/Dextran-Coated Silanized Nanomagnetic Particle by-Products The first high-field magnetic wash supernatant from Example 1, above, the magnetic particles in which had a hydrodynamic size of about 70 nm, was first subjected to HGMS purification using a commercially available HGMS 'XS' column (Catalogue#130-041-202; Miltenyi Biotec, San Diego, Calif.), which is packed with small ferromagnetic beads in order to remove the excess coating reagents. The 'XS' column was positioned in a uniform magnetic field created by positioning a 2 inch×1 inch×0.25 inch thick 'North' face and an identically sized 'South' face magnet against each other. The 'XS' column/magnetic assembly was attached to a peristaltic pump to facilitate rapid automated processing of the nanomagnetic particles.

30 mL (12.5 mg iron) of the first high-field magnetic wash supernatant was HGMS purified into a low-ionic strength HEPES pH7.5 buffer. After removal of the 'XS' column from the uniform magnetic field and resuspension with 3 mL of HEPES pH7.5 buffer, about 90% of the particles were recovered based on iron content. These HGMS-purified nanomagnetic particles had a hydrodynamic diameter of 73 nm and were then conjugated to a rat anti-mouse CD4 antibody (Catalogue#100506; BioLegend Inc., San Diego, Calif.) using heterobifunctional coupling chemistry. Briefly, the HGMS-purified 73 nm BSA/Dextran-coated nanomagnetic particles were activated with a SMCC cross-linker (Catalogue#51534; ThermoFisher Scientific, San Diego, Calif.) and conjugated to the rat anti-mouse CD4 antibody which had been thiolated using 2-Iminothiolane (Catalogue#26101; ThermoFisher Scientific, San Diego, Calif.). The final hydrodynamic size of these antibody-conjugated nanomagnetic particles was measured to be 83 nm. Although not thoroughly optimized, when this conjugated particle was used for targeting mouse $CD4^+$ cells from splenocyte cell suspensions in conjunction with 'MS'-type HGMS columns (Catalogue#130-042-201; Miltenyi Biotec Inc., Auburn, Calif.), purities and yields in excess of 90% were obtained as measured by flow cytometry with appropriate fluorescently labeled antibodies (FACSCalibur with CellQuest software; BD Biosciences, San Diego, Calif.).

These results show that these smaller particles, as compared to the larger ones described elsewhere herein, can also be effectively conjugated and utilized for isolation of biological materials.

4. Colloidal Stability of Streptavidin-Conjugated Nanomagnetic Particles

A 115 nm diameter BSA/Dextran-coated nanomagnetic particle produced according to Example 1, above, was conjugated covalently to Streptavidin as per the methods described in Example 3, above, to produce 135 nm diameter Streptavidin-conjugated nanomagnetic particles. Particle size measurements were carried out at various time points after resuspending and storing the nanoparticles in a high ionic strength solution (1 M NaCl) at room temperature. Control size measurements were carried out on the same nanoparticles in their normal storage buffer, which was a low-ionic strength buffer supplemented with BSA and sodium azide. Table 2, below, shows the results of this study. This study demonstrates significant resistance to aggregation and enhanced colloidal stability of the nanomagnetic particles of this invention.

TABLE 2

| Particle Size Stability in 1M Sodium Chloride | | | |
|---|---|---|---|
| STORAGE SOLUTION | SIZE @ 0 HOURS | SIZE @ 1 HOUR | SIZE @ 72 HOURS |
| Normal Storage Buffer | 135 nm | 137 nm | 137 nm |
| 1M Sodium Chloride | 139 nm | 139 nm | 140 nm |

5. Magnetic Separation Efficiency of Nanomagnetic Particles of the Invention

Figure 2:
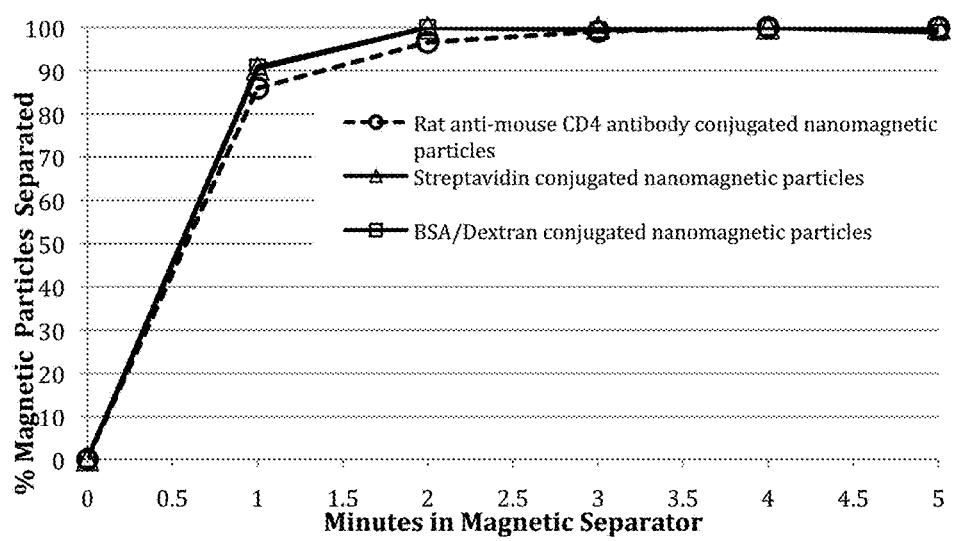
FIG. 2 shows the magnetic separation efficiency of various nanomagnetic particles made according to this invention.

FIG. 2 shows the magnetic separation efficiency of various nanomagnetic particles made according to this invention, which particles include a 113 nm diameter BSA/Dextran coated, a 127 nm antibody-conjugated particle, and a 130 nm Streptavidin-conjugated particle, the latter two of which are conjugated using the method described in Example 3, above. This study was performed using quadrupole magnetic separator built as described in U.S. Pat. No. 5,186,827 and designed to fit standard 12 mm×75 mm disposable laboratory test-tubes with dilute nanomagnetic particle suspensions containing 25 ug/mL iron in a physiological buffer such as an isotonic phosphate buffered saline solution. Similar strong magnetic separators for use with test-tubes are available from StemCell Technologies (Part #18000; Vancouver, British Columbia, Canada). FIG. 2 shows that all these aforementioned nanomagnetic particles separate rapidly and quantitatively within just a few minutes.

Figure 3:
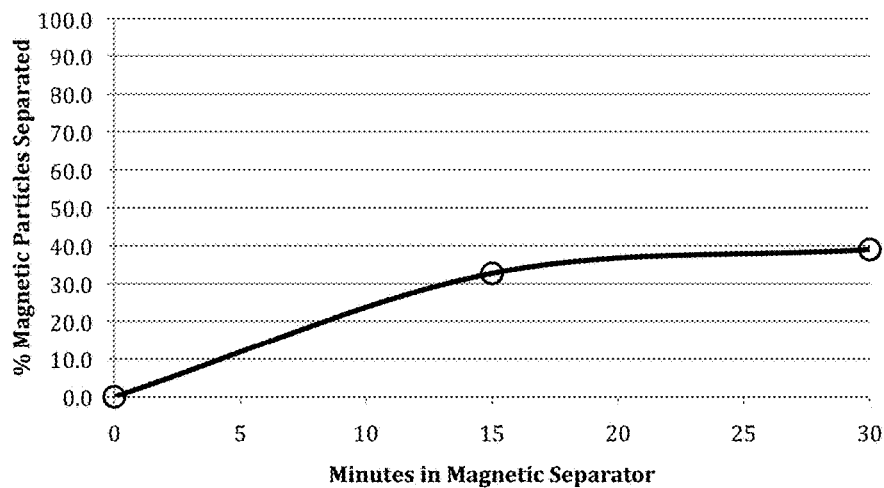
FIG. 3 shows the magnetic separation efficiency of an antibody-conjugated commercially available nanobead product.

Antibody-conjugated commercially available microbeads (Catalogue#130-049-201; Miltenyi Biotec Inc., Auburn, Calif.) having a measured hydrodynamic diameter of 82 nm were also tested for magnetic separation efficiency in the quadrupole magnetic separator, and the results shown in FIG. 3. As shown in FIG. 3, these 82 nm microbeads did not quantitatively separate at all in the quadrupole magnetic separator described above in this example. Instead, only about 40% of those magnetic particles could be separated after 30 minutes. These results demonstrate that those types of microbeads are only suitable for use with HGMS column-based magnetic separation methods. The nanomagnetic particles of the present invention, however, are suitable for quantitative magnetic particle-based separations in both external-field (dipole, tripole, quadrupole, hexapole type) as well as internal-field (HGMS)-based magnetic separators.

This property represents a significant differentiator in terms of practical utility of the nanomagnetic particles described in this specification, as no other magnetic particles are presently known to the inventors to function in both internal and external types of magnetic separators.

6. Non-Specific Binding of Nanomagnetic Particles to Mammalian Cells

Table 3, below, shows the non-specific binding (NSB) of different lots of BSA/Dextran-coated nanomagnetic particles synthesized over a 6 month period according to Example 1, above. In this study, mouse splenocytes ($1\times10^7$ total cells per tube) were incubated for 20 minutes at 4° C. with a relatively large number of nanomagnetic particles (about 2000 particles/cell or $2\times10^{10}$ total number of particles per sample). The cell/nanomagnetic particle reaction mixture was then magnetically washed twice with the aid of a quadrupole magnetic separator using just 5 minute magnetic separation times.

The washing steps were performed as follows: the cell suspension was diluted to a total volume of 4 mL with an isotonic PBS/BSA/EDTA buffer (5× Phosphate buffered saline (PBS), pH 7.2, 2.5% (w/v) Bovine Serum Albumin (BSA), and 10 mM EDTA) and the tube placed into a quadrupole-magnetic separator for 5 minutes. The supernatant was then discarded by gentle inversion of the magnetic separator or by aspiration with the aid of a pasteur pipette. The tube was then removed and its contents resuspended again with 4 mL of the isotonic buffer and placed back into the magnetic separator for another 5 minute separation. After the second aspiration, the cells were centrifuged and the cell pellet was resuspended with a small volume of isotonic buffer and then analyzed for the presence of non-specifically collected cells. The magnetically collected cells were then centrifuged once (5 minutes at 300×g) to remove excess or free nanomagnetic particles. The number of magnetically collected cells was then counted using an automated cell counter (Cellometer® VISION Trio; Nexcelom Bioscience, Lawrence, Mass.) which, together with the starting number of cells, enabled calculation of the percentage of cells that were magnetically selected (which is referred to as non-specific binding). Note that $2 \times 10^{10}$ particles is equivalent to a mass of about 40 ug of iron. More typically, for the efficient isolation of cells in high purity and yield, only about 10 ug to 20 ug of nanomagnetic particles (in terms of iron weight) need to be added for a sample containing $1 \times 10^7$ total cells.

These non-specific binding experiments were also repeated using high gradient magnetic separation (HGMS) columns (Part #130-042-201; MS-Columns; Miltenyi Biotec Inc., Auburn, Calif.) in place of the test-tube quadrupole magnetic separator (see Table 3, below). Due to the very high magnetic field gradients generated in such HGMS column separators, the nanomagnetic particle-to-cell ratio was drastically reduced to about 20 particles per 1 cell, or about $2 \times 10^8$ particles per sample. It was discovered that particle-to-cell ratios from 10:1 to 50:1 provide optimal target cell yields and purities (see Tables 5 and 6, below).

These studies were performed with a commonly used standard, cell compatible buffer (PBS) supplemented with 0.5 wt % BSA, 2 mM EDTA, and 0.1 wt % Casein and adjusted to pH 7.2.

TABLE 3

| Particle Lot # | Particle Diameter (nm) | Magnetic Separation Method | % Non-Specific Binding |
| --- | --- | --- | --- |
| MAG05 | 110 | Quadrupole | 1.1 |
| MAG06 | 113 | Quadrupole | 1.5 |
| MAG07 | 110 | Quadrupole | 1.9 |
| MAG08 | 105 | Quadrupole | 1.1 |
| MAG09 | 114 | Quadrupole | 1.4 |
| MAG10 | 114 | Quadrupole | 1.1 |
| MAG05 | 110 | MS Column | 1.1 |
| MAG06 | 113 | MS Column | 1.0 |
| MAG07 | 110 | MS Column | 1.0 |
| MAG08 | 105 | MS Column | 1.2 |
| MAG09 | 114 | MS Column | 0.8 |
| MAG10 | 114 | MS Column | 1.1 |

The non-specific binding (NSB) results in Table 3, above, with the nanomagnetic particles of this invention are extremely low, making it possible to attain target cell purities of up to about 99%. Most, if not all of currently available commercial magnetic particles cannot attain such low levels of NSB.

7. Specific Binding and Capture of Mammalian Cells Using a Quadrupole Magnetic Separator Compared to HGMS Separators Table 4, below, shows the titration results of a 127 nm diameter rat anti-mouse CD4 antibody-(Clone RM4-5; catalogue#100506; BioLegend Inc., San Diego, Calif.) conjugated nanomagnetic particle (prepared as described in Example 3, above) with mouse splenocytes. This titration was performed using particle-to-cell ratios from 500:1 to 1500:1. The protocol used was essentially identical to that described above in Example 6, above, except that after removal of excess nanomagnetic particles, an additional incubation with appropriate fluorochrome-conjugated antibodies (for phenotyping purposes) was carried out and the cells analyzed on a flow cytometer (FACSCalibur with CellQuest software; BD Biosciences, San Diego, Calif.) to determine the percent purity of the magnetically selected cells.

TABLE 4

| Particle-to-Cell Ratio | % Purity | % Yield |
| --- | --- | --- |
| 500:1 | 93.0 | 91.2 |
| 750:1 | 91.6 | 90.2 |
| 1000:1 | 92.6 | 92.9 |
| 1200:1 | 92.1 | 95.1 |
| 1500:1 | 89.3 | 90.7 |

This study clearly illustrates the biomedical utility of the nanomagnetic particles of this invention for isolating target cells of interest in high yield and purity for further interrogation.

Table 5, below, shows the results of a similar titration study done using the same 127 nm diameter rat anti-mouse CD4 antibody-conjugated nanomagnetic particle with mouse splenocytes; however, in this study, HGMS columns were used for performing the magnetic wash steps. As described to earlier (in Example 6, above), lower particle-to-cell ratios, from 5:1 to 50:1, were used in this HGMS based study.

Table 6, below, shows the results of a similar titration study done also using HGMS columns but with a 129 nm diameter rat anti-mouse CD19 antibody—(Clone 6D5; catalogue#115502; BioLegend Inc., San Diego, Calif. 92121) conjugated nanomagnetic particle (prepared as described in Example 3, above) in order to demonstrate the versatility of the nanomagnetic particles of the invention in HGMS-based cell isolation protocols.

TABLE 5

| Particle-to-Cell Ratio | % Purity | % Yield |
| --- | --- | --- |
| (rat anti-mouse CD4) | | |
| 5:1 | 90.1 | 55.9 |
| 10:1 | 92.5 | 84.9 |
| 20:1 | 88.9 | 95.8 |
| 30:1 | 84.5 | 98.6 |
| 40:1 | 84.2 | 99.1 |
| 50:1 | 83.0 | 99.2 |

TABLE 6

| Particle-to-Cell Ratio | % Purity | % Yield |
|---|---|---|
| (rat anti-mouse CD19) | | |
| 10:1 | 98.1 | 82.1 |
| 20:1 | 97.8 | 96.5 |
| 30:1 | 97.4 | 98.0 |
| 40:1 | 96.7 | 98.4 |
| 50:1 | 96.6 | 97.9 |

Both of these studies yielded excellent results for the purity and yield of the magnetically (purified) captured target cells across a relatively wide range of particle to cell ratios.

A commercially available magnetic particle was measured to have a hydrodynamic diameter of 170 nm and was also titrated as described in this example, with the results being shown in Table 7, below.

TABLE 7

| Particle-to-Cell Ratio | % Purity | % Yield |
|---|---|---|
| 10:1 | 93.7 | 88.7 |
| 15:1 | 91.0 | 60.0 |
| 20:1 | 95.2 | 62.0 |
| 30:1 | 93.9 | 37.0 |

This commercially available magnetic particle did not exhibit a sufficiently wide particle-to-cell usage ratio such that reliable and reproducible results could be obtained, therefore indicating that such conventional magnetic particles are not compatible for use with HGMS-type magnetic separation methods. The rapid loss of yield upon titration with those magnetic particles was most likely due to entrapment of the relatively large sized magnetic particles in the metallic (or ferromagnetic) matrix in the HGMS column, leading to inefficient recoveries of the magnetically labeled cells retained on the de-magnetized HGMS column. As those in the art will appreciate, such conventional magnetic particles can only be practically used with strong external-field magnetic separators such as the quadrupole-type magnetic separators used in the studies described above.

8. Stability of the Nanomagnetic Particles Produced According to Examples 1 and 3, Above To assess the long-term stability of the nanomagnetic particles of this invention, both Streptavidin- and rat anti-mouse CD19 antibody-conjugated particles were prepared according to Examples 1 and 3, above. Multiple small aliquots of these particles were then stored at three different temperatures (4° C., 25° C., and 37° C.) and magnetic cell separation tests were performed at various time points over the course of two months in order to monitor the overall biostability of these nanomagnetic particles. BioLegend's MojoSort™ Mouse CD4 T Cell Isolation Kit (Catalogue#480005) is a negative selection test that uses Streptavidin nanomagnetic particles in conjunction with a cocktail of biotinylated antibodies in order to magnetically select all cells that are CD4 negative. Additionally, BioLegend's MojoSort™ Buffer and MojoSort™ Magnet were used in the execution of the cell selection protocols described in this example. The "untouched" cells or supernatant from the magnetic separation step contained the desired CD4-positive cells. These "untouched" cells were then analyzed on a flow cytometer (FACSCalibur with CellQuest software; BD Biosciences, San Diego, Calif.) in order to determine the purity and yield of the targeted CD4-positive cells. Similar analyses were also performed using BioLegend's MojoSort™ Mouse CD19 Nanobeads (BioLegend, Catalogue#480001), which are rat anti-mouse CD19 antibody-conjugated nanomagnetic particles used to positively select CD19-positive cells.

Figure 4:
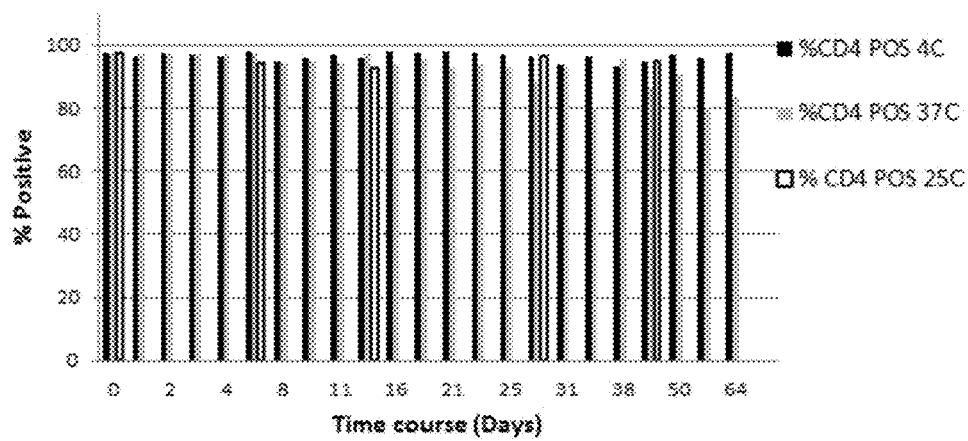
FIG. 4 shows the purity of CD4 positive cells that were negatively selected using Streptavidin-conjugated nanomagnetic particles and appropriate biotinylated antibodies that were stored at various temperatures and then tested for cell separation performance over the course of two months.
Figure 5:
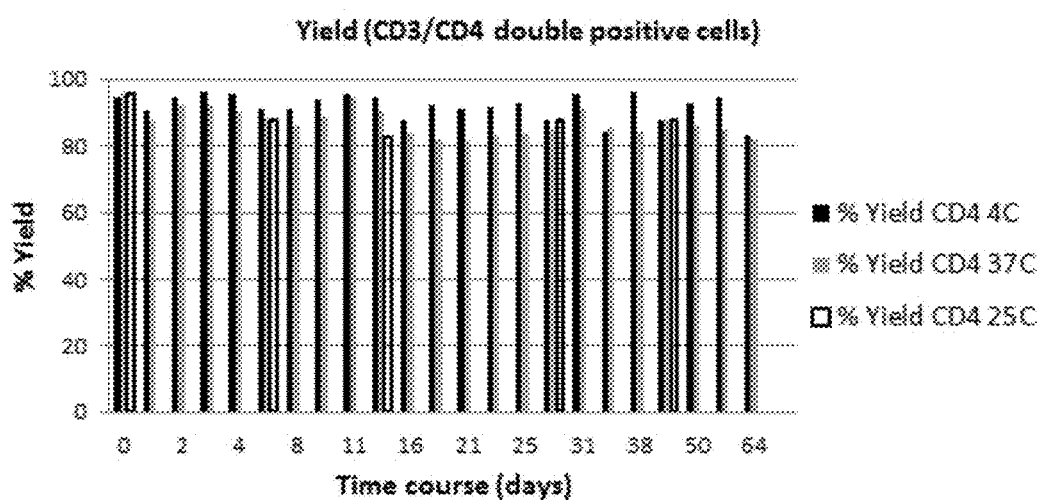
FIG. 5 shows the CD4 positive cell yield of Streptavidin-conjugated nanomagnetic particles that were stored at various temperatures and tested for cell separation performance as in FIG. 4 over the course of two months.

FIGS. 4 and 5 show the purity and yield, respectively, of CD4 positive cells that were negatively selected using Streptavidin nanomagnetic particles and appropriate biotinylated antibodies that were stored at various temperatures and tested for cell separation performance over the course of two months.

Figure 6:
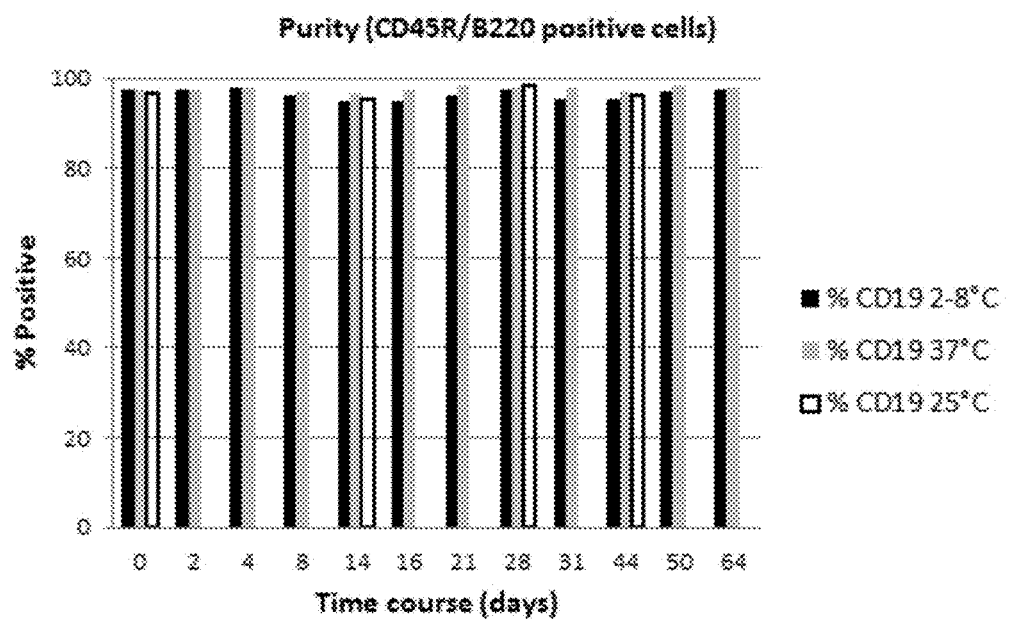
FIG. 6 shows the purity of rat anti-mouse CD19 antibody-conjugated nanomagnetic particles that were stored at various temperatures and tested for CD19 positive cell separation performance over the course of two months.
Figure 7:
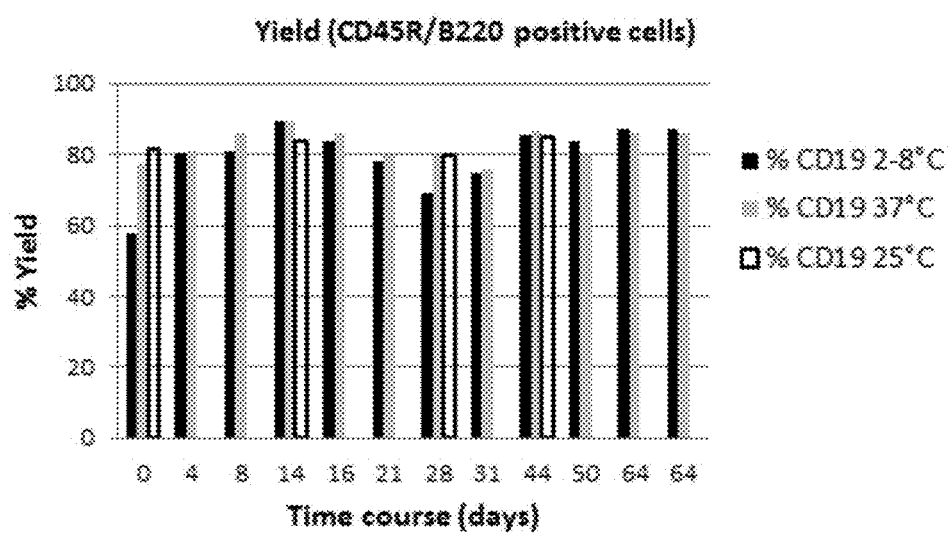
FIG. 7 shows the yield of rat anti-mouse CD19 antibody-conjugated nanomagnetic particles that were stored at various temperatures and tested for CD19 positive cell separation performance over the course of two months.

Similarly, FIGS. 6 and 7 show the purity and yield, respectively, of rat anti-mouse CD19 antibody conjugated nanomagnetic particles that were stored at various temperatures and tested for cell separation performance over the course of two months. Note that a non cross-reacting, fluorescently labeled B-cell-specific antibody called CD45R/B220 (Catalogue#103223; BioLegend Inc., San Diego, Calif.) was used to identify the magnetically selected B cells.

The results of these stability studies clearly demonstrates the excellent biostability of the nanomagnetic particles of the invention. The fact that both sets of nanomagnetic particles used in these studies have at least 30 or more days of biostability at an elevated temperature of 37° C., which can be extrapolated to upwards of more than 4 years of biostability at 4° C., can be attributed to the patentable nanomagnetic particle composition and synthesis designs presented in this specification. In contrast, conventional magnetic particles ranging in size from 80 nm to 1000 nm have been reported to have shelf-lives or biostability in the range of a few months to about 20 months even when refrigerated at 4° C.

9. Comparison of Particle Size Distributions

Figure 8:
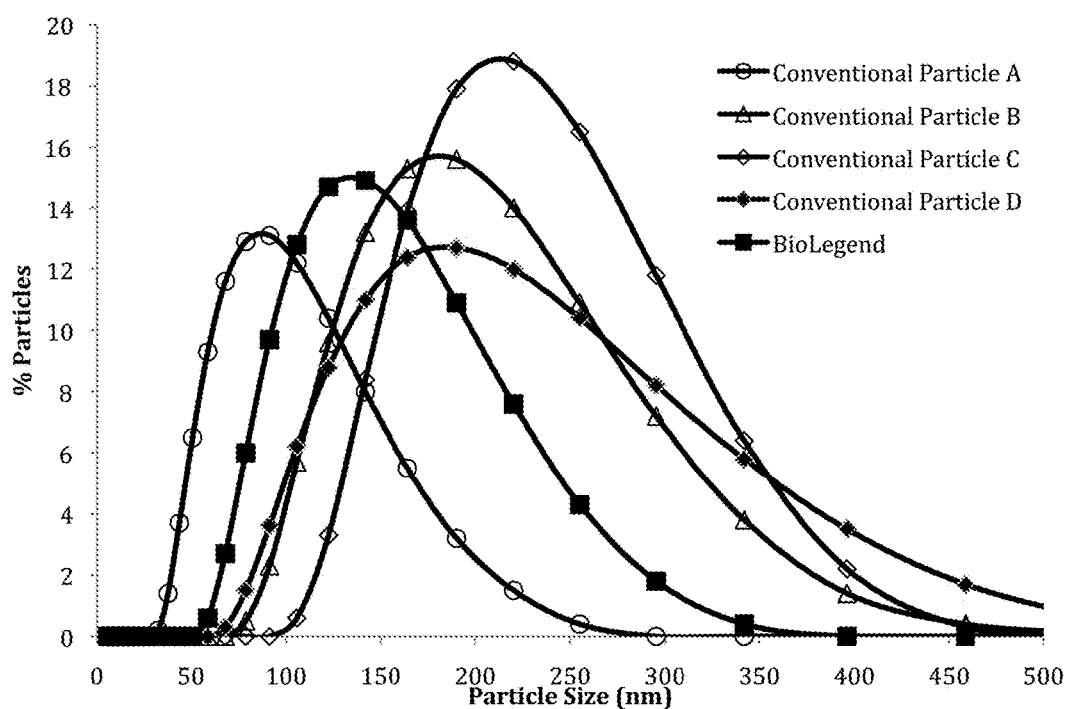
FIG. 8 is a plot showing the particle size distributions of various conventional, commercially available magnetic particles compared to those of the invention produced in accordance with Example 1, below. Measurements were made using dynamic light scattering and the percentage of particles in various 'size-bins' was plotted as a function of actual particle size.

The particle size distributions of various conventional, commercially available magnetic particles that are highly utilized in the targeted cell separations market were measured and compared to those produced using Example 1, above. These measurements were made using dynamic light scattering (Malvern Nano-S ZetaSizer; Westborough, Mass.), and the percentage of particles in various 'size-bins' was plotted as a function of actual particle size, as shown in FIG. 8. Hydrodynamic diameters are measured on a Malvern Nano-S ZetaSizer instrument that uses the principles of 'dynamic light scattering' whereby particles are illuminated with a laser and the scattered light analyzed for intensity fluctuations. The nanomagnetic particles of the invention (labeled as "BioLegend" in FIG. 8) had a hydrodynamic diameter of about 130 nm and relatively insignificant numbers of particles greater than about 300 nm in diameter (an important criterion in order for magnetic particles to perform equally well in both 'external-field' and 'internal-field' based magnetic separators). Note that the particles labeled "Conventional Particle 'A'" in FIG. 8 had a hydrodynamic diameter of about 82 nm and therefore would only be suitable for use with 'internal-field' generating or HGMS columns (see FIG. 3, above, also).

10. Transmission Electron Microscopy of Cells Selected Using HGMS

Figure 9:
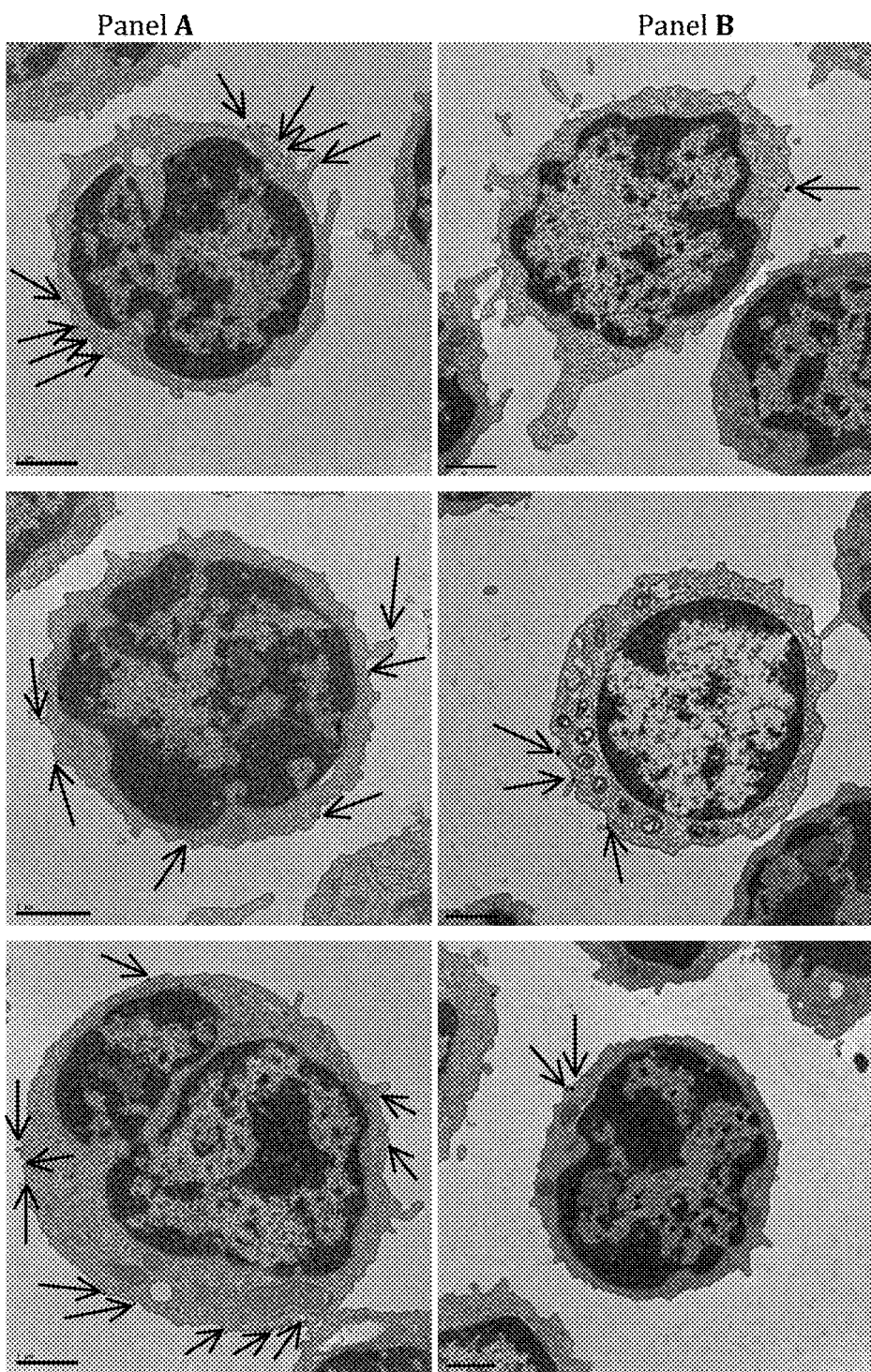
FIG. 9 has two panels, A and B, each of which contain 3 transmission electron micrographs. The micrographs in Panel A show cells magnetically selected by HGMS using commercially HGMS compatible magnetic particles, while the micrographs in Panel B show cells magnetically selected by HGMS using targeted nanomagnetic particles of the present invention.

In this study, cells were magnetically selected by HGMS using both commercially HGMS compatible magnetic particles (FIG. 9, Panel A) and targeted nanomagnetic particles of the present invention (FIG. 9, Panel B). The representative electron micrographs shown in FIG. 9 were produced using 55 nm cryosections of the magnetically selected cells and imaged on a Transmission Electron Microscope. A single cell suspension from C57BL/6 mouse spleen was prepared to isolate CD19+ B cells using the MojoSort™ Mouse CD19 Nanobeads (BioLegend, CA) and commercial mouse CD19 MicroBeads (Miltenyi, Germany) followed by BioLegend and Miltenyi recommended protocol. Isolated CD19 cell purity (97% from BioLegend, 94.9% from Miltenyi) was identified by staining of the resulting cells with CD45R/B220 (clone RA3-6B2) PE and analysis by flow cytometry. Then the cells were centrifuged and the cell pellets were resuspended in a modified Karnovsky's fixative (2.5% glutaraldehyde and 2% paraformaldehyde in 0.15 M sodium cacodylate buffer, pH 7.4) for 4 hours. Then the preparation was post-fixed in 1% osmium tetroxide in 0.15 M cacodylate buffer for 1 hour and stained en bloc in 2% uranyl acetate for 1 hour. Samples were then dehydrated in ethanol, embedded in Durcupan epoxy resin (Sigma-Aldrich), sectioned at 50 to 60 nm on a Leica UCT ultramicrotome, and picked up on formvar and carbon-coated copper grids. Sections were stained with 2% uranyl acetate for 5 minutes and Sato's lead stain for 1 minute. Grids were then viewed on a JEOL 1200EX II (JEOL, Peabody, Mass.) transmission electron microscope and photographed using a Gatan digital camera (Gatan, Pleasanton, Calif.), or viewed using a Tecnai G2 Spirit BioTWIN transmission electron microscope equipped with an Eagle 4k HS digital camera (FEI, Hilsboro, Oreg.).

Similarly low numbers of the targeted nanomagnetic particles of the invention compared to those of conventional labeled magnetic particles were observed across 40 images from each sample type. These electron micrographs clearly show that far fewer of targeted nanomagnetic particles of the invention are bound to the target cells than in the micrographs showing cells bound by conventional labeled magnetic particles. The arrows in these micrographs mark the location of visualizable magnetic particles on the surface of these cells. This (the ability to mediate magnetic separation with very few nanomagnetic particles per cell) is a very important attribute of the targeted nanomagnetic particles of the present invention because such magnetically selected cells are essentially in a "native" or "untouched" state with very little, if any, perturbation of the cell's biological processes. This allows the cells to be captured in a biologically intact and responsive state (see Example 12).

11. Nanomagnetic Particle Lyophilization Studies

Mouse anti-CD19 conjugated nanobeads ($2\times10^8$ total particles) and SAv conjugated nanobeads ($2\times10^8$ total particles) produced according to Examples 3 and 4, above, respectively, were suspended in various supplemented solutions and subjected to a 3 day lyophilization (Lyo) cycle on a Genesis Pilot Lyophilizer (SP Scientific). Specifically, particle suspensions contained in silanized glass vials were frozen down to −46° C., then to −80° C. for 3 hours and back to −46° C. and kept in a sealed vacuum chamber for 3 days. Thereafter, the temperature was raised to 22° C. The lyophilized nanomagnetic particles were then reconstituted with PBS and tested for performance using both the MojoSort™ Mouse CD19 Nanobeads (BioLegend Inc., San Diego, Calif.; catalogue #480001) and the MojoSort™ Mouse CD4 T Cell Isolation Kits (BioLegend Inc., San Diego, Calif.; catalogue #480005). The results shown in Tables 8 and Table 9, respectively, below.

TABLE 8

Mouse CD19 positive selection purity and yield by using reconstituted lyophilized (lyo) CD19 nanobeads

| Particles | Purity (%) | Yield (%) |
| --- | --- | --- |
| Non Lyophilized 6D5 particle (Control) | 97.7 | 82 |
| 6D5 nanobeads in Storage Buffer (Lyo) | 97.1 | 72 |
| in 1% BSA (Lyo) | 96.9 | 88 |
| in 1% Dextran (Lyo) | 96.9 | 88.2 |
| in 2% Sucrose (Lyo) | 97 | 89.2 |
| in 1% Dextran + 1% Sucrose (Lyo) | 96.7 | 90.8 |

TABLE 9

Mouse CD4 negative selection purity and yield by using reconstituted lyophilized (lyo) SAv particles

| Particles | Purity (%) | Yield (%) |
| --- | --- | --- |
| Non lyophilized SAv (Control) | 95.4 | 90.0 |
| in 1% BSA (Lyo) | 92.8 | 92.9 |
| in 1% Dextran (Lyo) | 96 | 88.1 |
| in 2% Sucrose (Lyo) | 96 | 87.0 |
| in 1% Dextran + 1% Sucrose (Lyo) | 96.2 | 87.6 |

These lyophilized and reconstituted nanomagnetic beads show excellent retention of bioactivity, indicating that lyophilization facilitates extended storage/stability of the targeted nanomagnetic beads of the invention for very long periods of time.

12. Functional Studies of Magnetically Selected Cells

Magnetically selected cells are often used for downstream processing such as gene/protein/RNA profiling; however, many if not most of commercially available magnetic particles have a toxic effect on cells, Therefore, it is quite challenging to obtain live or viable cells with magnetic particles attached to them for further studies/probing. In this study, both a targeted nanomagnetic particle of the invention and a widely used commercially available magnetic particle conjugated to an antibody against the mouse CD4 antigen were tested side-by-side for cell functionality after the target CD4+ cells were magnetically isolated.

Briefly, a rat anti-mouse CD4 antibody (Clone RM4-5; catalogue#100506; BioLegend Inc., San Diego, Calif.) conjugated nanomagnetic particle (prepared as described in Example 3, above) was tested alongside anti-CD4 (Clone L3T4; Catalogue#130-049-201; Miltenyi Biotec Inc., Auburn, Calif.) conjugated microbeads using HGMS columns (Catalogue#130-042-201; Miltenyi Biotec Inc., Auburn, Calif.). The anti-CD4-conjugated nanomagnetic particles of the invention had a hydrodynamic diameter of 127 nm whereas the L3T4-conjugated microbeads had a hydrodynamic diameter of 82 nm. Table 10, below, shows the purity and yield of the isolated CD4+ cells from both types of these magnetic particles when used for isolating CD4+ cells from a mouse spleen according to the manufacturer's instructions.

TABLE 10

| Type of nanomagnetic particle used | % PURITY | % YIELD |
| --- | --- | --- |
| BioLegend anti-CD4 nanobeads | 92.4 | 65 |
| MACS anti-CD4 MicroBeads | 91.5 | 67 |

Figure 10:
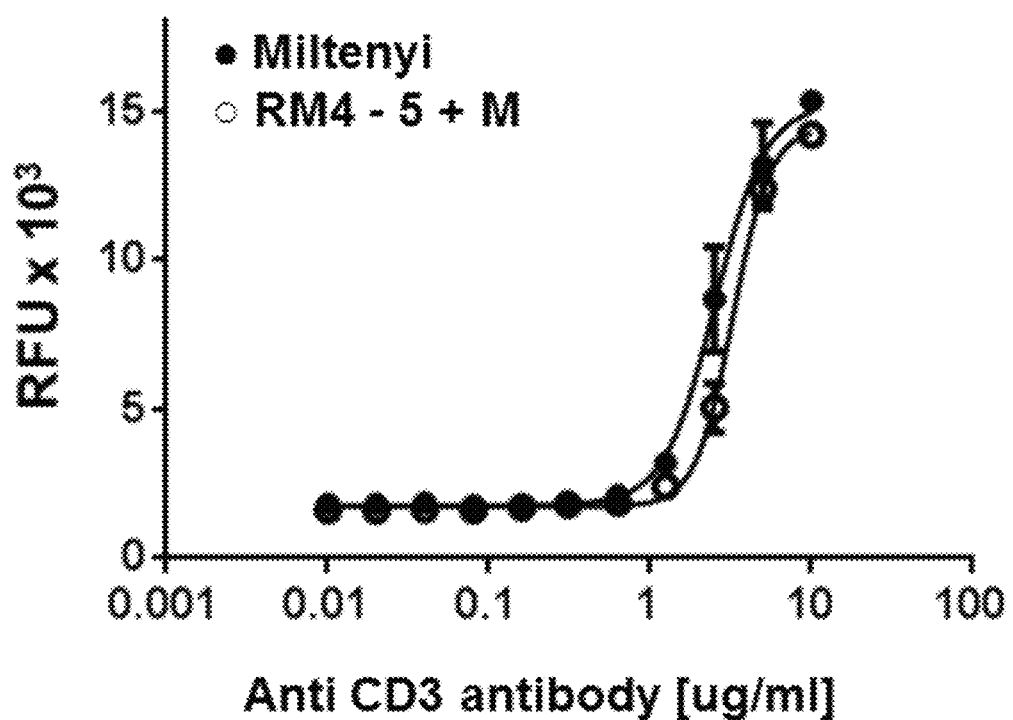
FIG. 10 shows a plot of relative fluorescence units (RFU) versus concentration of anti-mouse CD3 antibody used for coating microwells to drive the cells to proliferate. RFU is an index of the relative number of cells in each condition.

After magnetic isolation of the CD4+ cells, equal amounts of CD4+ cells ($1\times10^6$ cells) from both isolation methods were seeded into 96-well microplates coated with mouse anti-CD3 (Clone 17A2; catalogue#100201; BioLegend Inc., San Diego, Calif.) antibody in varying concentrations and supplemented with 1 ug/mL soluble mouse anti-CD28 (Clone 37.51; catalogue#102101; BioLegend Inc., San Diego, Calif.) and incubated for 3 days at 37° C. Next, a solution of the fluorescent redox marker resazurin (catalogue# TOX8-1KT; SIGMA-ALDRICH; St. Louis, Mo.), which measures the metabolic activity of living cells, was added into the wells at a 10% volume ratio and the relative fluorescence intensity was measured after a 7 hour incubation using a SPECTRAmax Gemini XPS fluorescence microplate reader (Molecular Devices, Sunnyvale, Calif.). A plot of the relative fluorescence units (RFU) versus the concentration of the anti-mouse CD3 antibody used for coating the microwells is shown in FIG. 10. Note that in FIG. 10, the higher the fluorescence intensity, the higher the number of living cells.

The results of this functional cell assay clearly demonstrates that the nanomagnetic particles of the present invention do not have a significant toxicological effect on the magnetically selected cells even though these nanomagnetic particles are larger than the tested commercial magnetic microbeads.

13. Combined Use of Microbubbles in Conjunction with Nanomagnetic Particles for Cell Isolation Micro-sized buoyant bubbles are hollow (or air-filled) micron-sized spheres that are commercially available with functionalized surfaces or coated ligands for targeting moieties of interest. Commercially available examples that could be conjugated with cell-specific ligands (e.g., cell antigen specific antibodies) and used to isolate specific cell populations include the gas-encapsulated microbubbles from Targeson (San Diego, Calif.) and Buoyant Microbubbles from Akadeum Life Sciences (Ann Arbor, Mich.). Examples described in the research literature include the perfluorocarbon microbubbles of Shi, et al., Methods, 64, 102 (2013), glass microbubbles of Hsu, et al., Technology (Singapore World Science), 3, 38 (2014), albumin microbubbles of Liou, et al., *PLoS One*, 20, 10 (2015), and gas-filled immune-microbubbles of Shi, et al., *PLoS One*, 8, 1 (2013). Examples of patent literature describing the use of microbubble-based systems for isolation of analytes or cells include U.S. patent and published patent application nos. 5116724, 5246829, 8835186, US 2003/0104359 A1, US 2007-0036722 A1, and US 2011/0236884 A1. These examples illustrate the value of using a buoyancy-based system for the specific isolation of target cells and analytes. Yet, prior to this invention, none have combined a buoyancy based system with magnetic nanoparticles to provide faster, more efficient and more effective isolation of the desired target(s).

Figure 11:
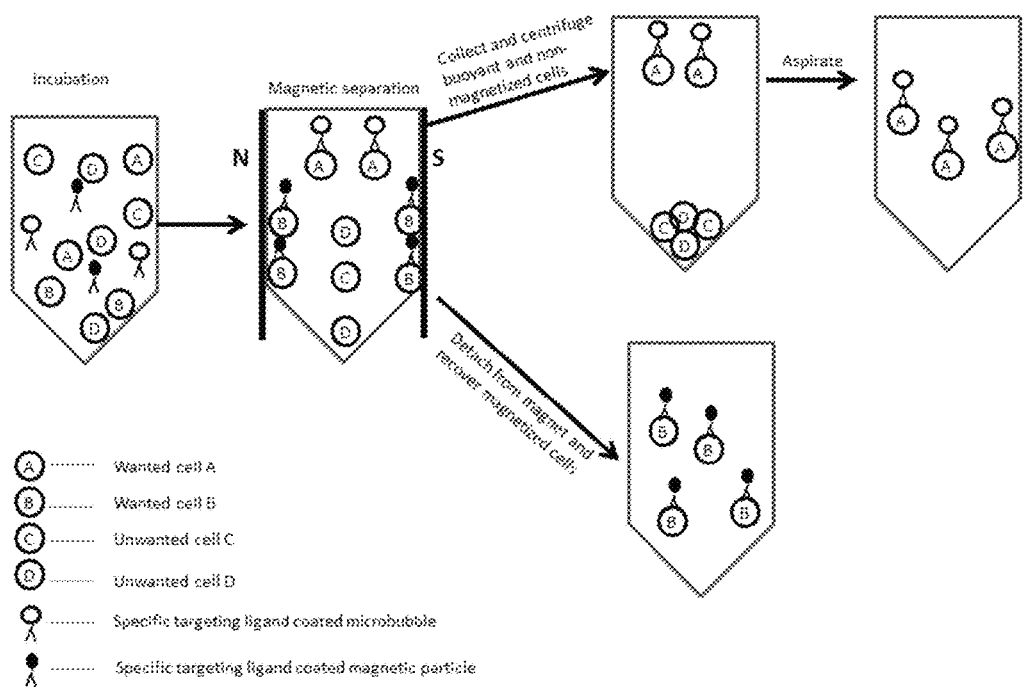
FIG. 11 illustrates the general scheme for "magnetibuoyant" separation methods of the invention.

In this example, a patentable method is described wherein both targeted microbubbles, of any composition, and targeted nanomagnetic particles, of any composition, can be used sequentially and/or simultaneously to obtain one, two, or three cell populations of interest. A combination of magnetic and buoyant isolation, or "magnetibuoyant", procedures will allow difficult separations to be achieved. Such "magnetibuoyant" methods of cell isolation significantly reduce the time and resources required to isolate different cells of interest, and the populations can be obtained at very high purities. The magnetic nanoparticles of the present invention are particularly well suited for this application due to their high stability in various fluids, small size, more highly magnetically responsive property, ability to separate cells at lower particle to cell ratios as compared to other magnetic particles and capacity to respond quickly to magnetic fields as compared to other magnetic particles. These advantages have not previously been realized and/or commercialized. FIG. 11 illustrates the general principle.

Considering FIG. 11, if a mixture of different cell types (A, B, C, D) containing two desired subpopulations (A and B) are combined in a reaction mixture with microbubbles targeted to one cell type (A) and with magnetic particles targeted to a second type (B), then allowing the first set of A cells to float to the surface while the second set of B cells is drawn to a strong magnetic field (such as the quadrupole magnetic separator described in Example 5, above), this will cause the magnetized target cells to be separated at right angles to the levitation direction of the microbubble-targeted cells. In this manner both populations of cells can be isolated at the same time and can be harvested individually for further use from the same initial reaction mixture. In this simple example both of the different cell populations (A and B) may be desired for further use, and can be easily harvested. Alternatively, one population may be unwanted cells that will be discarded with, for example, the intent of removing them as potential contaminants of the second isolated population. And finally, the third "remainder" population (in this example, cell types C and D), i.e., those not targeted by either the microbubbles or the magnetic particles, may also be harvested for further use since that (those) population(s) can also be retained as the two targeted populations (A and B) are harvested.

Figure 12:
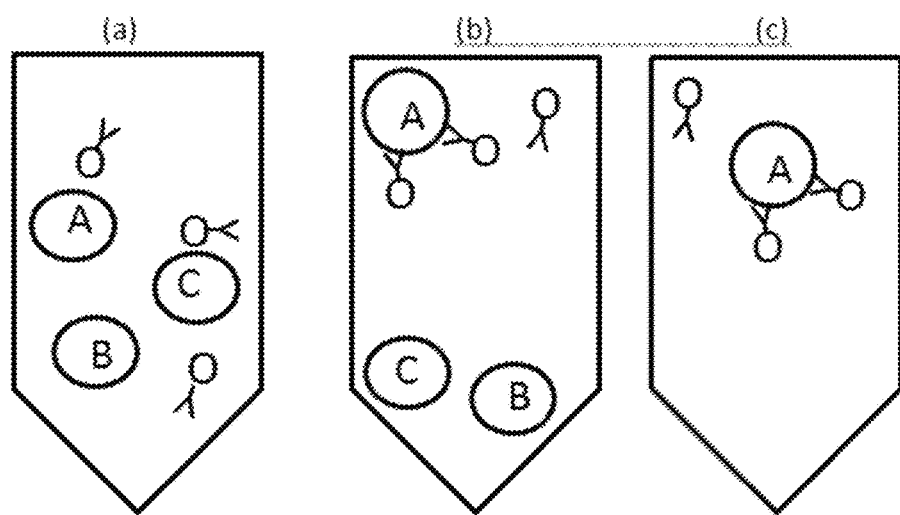
FIG. 12 illustrates the principle of using microbubbles to isolate specific cells.

As background, FIG. 12 illustrates the principle of using only microbubbles to isolate mouse CD19+ cells. In this example, rat anti-mouse CD19 conjugated (Clone 6D5; catalogue#115502; BioLegend Inc., San Diego, Calif.) microbubbles (prepared using the conjugation methods described in Example 3, above, except that centrifugation is used for all wash steps) are incubated with mouse splenocytes for 15 minutes at 4° C. in a small eppendorf tube on a rotator (see (a) in FIG. 12). The cell suspension is then transferred into a test tube and diluted up to a total volume of 4 mL with isotonic cell buffer and centrifuged for 5 minutes at 300×g (see (b), FIG. 12). The floating cells are then gently poured or aspirated and transferred into a new test-tube (see (c), FIG. 12). The cells are then stained with a fluorescent CD45R/B220 antibody conjugate (phycoerythrin conjugated rat anti-mouse/human CD45R/B220; catalogue#103207; BioLegend Inc., San Diego, Calif.), and the collected cells analyzed on a flow cytometer (FACSCalibur with CellQuest software; BD Biosciences, San Diego, Calif.). T able 11, below, shows the purity and yield of the mouse CD19+ target cells obtained using such antibody conjugated microbubbles.

TABLE 11

|  | Pre Isolation | Post Isolation |
|---|---|---|
| Purity | 55% | 98.6% |
| Yield | 100% | 92.4% |

Example i: Magnetibuoyant Methods for Rare Cell Isolation

Commercially available methods for isolating rare cells (i.e., cells such as stem cells, circulating tumor cells, fetal cells, endothelial cells, etc.) are magnetic particle-based, two-step protocols where a negative depletion step is carried out first to remove unwanted cells followed by washing steps and a positive selection step to capture rare cells. The direct positive selection of rare cells has only limited success due to non-specific binding of the solid-phase materials (i.e., magnetic and non-magnetic beads) and the immense difficulty in targeting and binding to these rare cells, which are present only at very low frequencies, typically at 1 target cell per 1 million (or more) total cells. Furthermore, the starting cell suspensions often used for direct positive selection of rare cells are very challenging cell preparations such as whole blood, buffy coats, and/or lysed whole blood. Any significant manipulation of the starting or native cell suspension has a negative impact on the recovery/yield of any rare cells present in the sample due to inherent cell losses experienced at every stage of cell sample processing.

Figure 13:
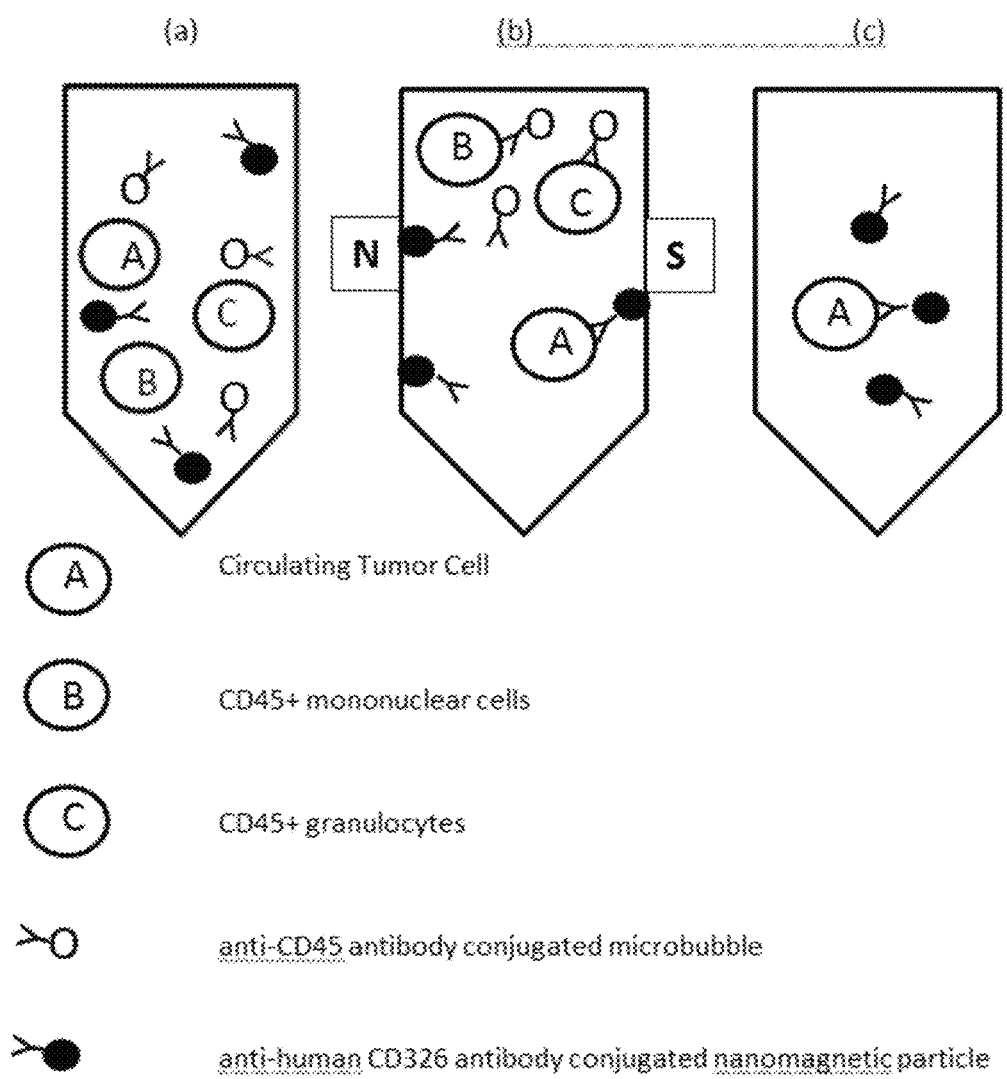
FIG. 13 illustrates the general scheme for "magnetibuoyant" rare cell separation methods of the invention.

FIG. 13 depicts a protocol for using CD45 antibody— (Clone 2D1-anti-human CD45; catalogue #368502; BioLegend Inc., San Diego, Calif.) conjugated microbubbles. The CD45 microbubbles are used in conjunction with a rare cell-specific, CD326 antibody (Clone 9C4-anti-human CD326 [EpCAM]; catalogue #324202; BioLegend Inc., San Diego, Calif.) that is conjugated to a nanomagnetic particle (preferably, a nanomagnetic particle prepared in accordance with this invention). Used together, the combination of particles allows the direct and efficient enrichment of circulating tumor cells in a single step.

In FIG. 13, (a) represents the reaction mixture in a standard tissue culture tube compatible with a commercially available magnetic separator. After an incubation step to allow the targeted buoyant and magnetic particle populations to bind to their respective target cells, the tube is inserted into a magnetic separator where the magnetic particles and cognate cells are drawn to the magnetic field on the walls of the tube, At the same time, the microbubbles levitate their cognate cells to the surface (b). With the tube still in the magnetic separator, the microbubble-associated cells can be aspirated or simply poured away without disturbing the magnetically retained cells. After decanting the tube (b) and removing it from the magnetic separator, a very pure suspension of these rare tumor cells is left behind in the tube (c) for further interrogation and studies.

Example ii: Magnetibuoyant Method for Isolating Human CD4+ Cells at Very High Purities The rationale depicted in FIG. 13 above can also be applied to the isolation of human CD4+ lymphocytes since the antibody targeting the CD4 antigen receptor is also co-expressed on monocytes. Current methods for isolating human CD4+ cells from peripheral blood mononuclear cells in high purity requires a pre-enrichment step to remove contaminating monocytes either with magnetic particles or by adherence to plastic plates. Thereafter, the CD4+ lymphocytes are isolated using anti-CD4 coated magnetic particles.

Figure 14:
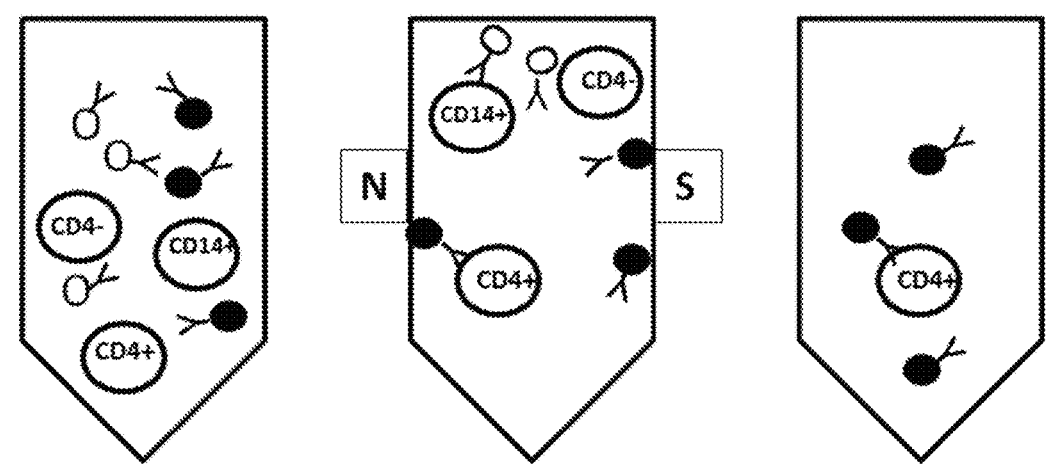
FIG. 14 illustrates the isolation of human CD4+ lymphocytes from a complex mixture.
Figure 14:
Figure 14:
Figure 14:
Figure 14:
Figure 14:

As shown in FIG. 14, a monocyte-specific antibody recognizing the monocyte marker CD14, such as clone #63D3 (catalogue #367102; BioLegend Inc., San Diego, Calif.), is conjugated to microbubbles and an anti-CD4-specific antibody, such as clone #5K3 (catalogue #344602; BioLegend Inc., San Diego, Calif.), is conjugated to nanomagnetic particles. With magnetibuoyant cell isolation the buoyant CD14/CD4 double positive monocytes are lifted away from the CD4 single positive T cells, which are captured to the walls of the tube with magnetic force. This results in a significant reduction in processing time and increased throughput can be realized.

Definitions

In the context of the invention described above and in the claims below, the following terms will be understood to have the meanings ascribed. In addition to these terms, others are defined elsewhere in the specification, as necessary. Unless otherwise expressly defined below or elsewhere in the specification, terms of art used in this specification will have their art-recognized meanings.

As used herein, the singular forms "a", "an", and "the" include plural references unless the context clearly dictates otherwise.

As used herein, the term "about" refers to approximately a +/−10% variation from the stated value. It is to be understood that such a variation is always included in any given value provided herein, whether or not it is specifically referred to.

An "analyte" refers to the substance to be detected, which may be suspected of being present in the sample (i.e., the biological sample). The analyte can be any substance for which there exists a naturally occurring specific binding partner or for which a specific binding partner can be prepared. Thus, an analyte is a substance that can bind to, or be bound by, one or more specific binding partners.

An "antibody" refers to a protein consisting of one or more polypeptides substantially encoded by immunoglobulin genes or fragments of immunoglobulin genes. This term encompasses polyclonal antibodies, monoclonal antibodies, and antigen-binding antibody fragments, as well as molecules engineered from immunoglobulin gene sequences that specifically bind an antigen of interest. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains, respectively.

Antibodies exist as intact immunoglobulins or as a number of well-characterized antigen-binding antibody fragments produced by digestion with various peptidases. Thus, for example, pepsin digests an antibody below the disulfide linkages in the hinge region to produce F(ab')$_2$, a dimer of Fab which itself is a light chain joined to VH-CH1 by a disulfide bond. The F(ab')$_2$ may be reduced under mild conditions to break the disulfide linkage in the hinge region thereby converting the (Fab')$_2$ dimer into a Fab' monomer. The Fab' monomer is essentially a Fab with part of the hinge region. While various antigen-binding antibody fragments are defined in terms of the digestion of an intact antibody, one of skill will appreciate that such Fab' fragments may be synthesized de novo either chemically or by utilizing recombinant DNA methodology. Thus, in the context of the invention the term "antibody" also includes antigen-binding antibody fragments either produced by the modification of whole antibodies or synthesized de novo using recombinant DNA methodologies. Antibodies include single chain antibodies (antibodies that exist as a single polypeptide chain), single chain Fv antibodies (sFv or scFv), in which a variable heavy and a variable light chain are joined together (directly or through a peptide linker) to form a continuous polypeptide. The single chain Fv antibody is a covalently linked VH-VL heterodimer that may be expressed from a nucleic acid including VH- and VL-encoding sequences either joined directly or joined by a peptide-encoding linker. While the VH and VL are connected to each as a single polypeptide chain, the VH and VL domains associate non-covalently. The scFv antibodies and a number of other structures convert the naturally aggregated, but chemically separated, light and heavy polypeptide chains from an antibody V region into a molecule that folds into a three dimensional structure substantially similar to the structure of an antigen-binding site are known to those of skill in the art.

A "binding partner" or "member" of a high affinity binding pair is a member of a binding pair, i.e., a pair of molecules wherein one of the molecules binds to the second molecule. Binding partners that bind specifically are termed "specific binding partners." A "high affinity" binding pair is one in which the members bind with high affinity. In addition to antigen and antibody binding partners commonly used in immunoassays, other specific binding partners can include biotin and avidin (or streptavidin), carbohydrates and lectins, nucleic acids with complementary nucleotide sequences, ligand and receptor molecules, cofactors and enzymes, enzyme inhibitors and enzymes, and the like. Furthermore, specific binding partners can include partner(s) that is/are analog(s) of the original specific binding partner, for example, an analyte-analog. Immunoreactive specific binding partners include antigens, antigen fragments, antibodies (monoclonal and polyclonal) and antigen-binding antibody fragments.

A "biological sample" is a sample of biological material taken from a patient or subject, as well as samples taken from tissue culture or tissue culture supernatants or any other source that could contain the analyte of interest. Biological samples include samples taken from bodily fluids and tissues (e.g., from a biopsy) or tissue preparations (e.g., tissue sections, homogenates, etc.). A "bodily fluid" is any fluid obtained or derived from a subject suitable for use in accordance with the invention. Such fluids include whole blood, blood fractions such as serum and plasma, urine, sweat, lymph, feces, ascites, seminal fluid, sputum, nipple aspirate, post-operative seroma, wound drainage fluid, saliva, synovial fluid, bone marrow, cerebrospinal fluid, nasal secretions, amniotic fluid, bronchoalveolar lavage fluid, peripheral blood mononuclear cells, total white blood cells, lymph node cells, spleen cells, and tonsil cells.

The terms "e.g.," "such as", and like terms mean "for example", and thus do not limit the term or phrase they explain, whereas the term "i.e.," and like terms mean "that is", thus limiting the term or phrase it explains.

As used herein, the term "epitope" or "epitopes," or "epitopes of interest" refer to a site(s) on any molecule that is recognized and is capable of binding to a complementary site(s) on its specific binding partner. The epitope-bearing molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody, e.g., an autoantibody. Typically an epitope is contained within a larger molecular framework (e.g., in the context of an antigenic region of a protein, the epitope is the region or fragment of the protein having the structure capable of being bound by an antibody reactive against that epitope) and refers to the precise residues known to contact the specific binding partner. As is known, it is possible for an antigen or antigenic fragment to contain more than one epitope.

"Herein" means in the present application, including anything that may be incorporated by reference.

The terms "including", "comprising", and variations thereof mean "including, but not necessarily limited to". Thus, for example, the phrase "the composition includes a drug and carrier" means the composition includes the drug and the carrier, but may also include one or more other unspecified components as well.

As used herein, "specific" or "specificity" in the context of an interaction between members of a specific binding pair (e.g., an antigen and antibody that specifically binds such antigen) refers to the selective reactivity of the interaction. The phrase "specifically binds to" and analogous terms refer to the ability of antibodies to specifically bind to (e.g., preferentially react with) an antigen and not specifically bind to other entities. Antibodies or antigen-binding antibody fragments that specifically bind to a particular antigen can be identified, for example, by diagnostic immunoassays (e.g., radioimmunoassays ("RIA") and enzyme-linked immunosorbent assays ("ELISAs"), surface plasmon resonance, or other techniques known to those of skill in the art. In one embodiment, the term "specifically binds" or "specifically reactive" indicates that the binding preference (e.g., affinity) for the target analyte is at least about 2-fold, more preferably at least about 5-fold, 10-fold, 100-fold, 1,000-fold, a million-fold or more over a non-specific target molecule (e.g., a randomly generated molecule lacking the specifically recognized site(s)).

The term "labeled" refers to a molecule (e.g., an antibody, nanoparticle, etc.) that is labeled with a detectable label or becomes labeled with a detectable label during use. A "detectable label" includes any moiety that is detectable or that can be rendered detectable. With reference to a labeled separable particle, a "direct label" is a detectable label that is attached to or associated with, covalently or non-covalently, the particle, and an "indirect label" is a detectable label that specifically binds the particle. Thus, an indirect label includes a moiety that is the specific binding partner of a moiety of the detection agent. Biotin and avidin are examples of such moieties that can be employed, for example, by contacting a biotinylated antibody with labeled avidin to produce an indirectly labeled antibody (and thus labeled nanomagnetic particle). A "label" refers to a detectable compound or composition, such as one that is conjugated directly or indirectly to a target-specific binding member. The label may itself be detectable by itself (e.g., a Raman label, a radioisotope, a fluorescent label, etc.) or, in the case of an enzymatic label, may catalyze chemical alteration of a substrate compound or composition that is detectable.

A "microparticle" refers to a small particle that is recoverable by any suitable process, e.g., magnetic separation or association, ultracentrifugation, etc. Microparticles typically have an average diameter on the order of about 1 micron or less.

A "nanoparticle" refers to a small particle that is recoverable by any suitable process, e.g., magnetic separation or association, ultracentrifugation, etc. Nanoparticles typically have an average diameter on the order of about 500 nanometers (nm) or less, preferably from about 20 nm to about 300 nm, or any size or size range within such 1 nm-about 500 nm size range.

A "patentable" process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

The terms "separated", "purified", "isolated", and the like mean that one or more components of a sample or reaction mixture have been physically removed from, or diluted in the presence of, one or more other components present in the mixture.

The term "species" is used herein in various contexts, e.g., a particular target biomolecule species. In each context, the term refers to a population of chemically indistinct molecules of the sort referred in the particular context.

REFERENCES

1. Massart, R., IEEE Trans. Magn., v17(2), p 1247-1248 (1981).
2. Schwertmann, U., Cornell, R. M., Iron Oxides in the Laboratory: Preparation and Characterization: VCH Publication (New York, N.Y.), ISBN:3527269916 (1991).
3. Wetzel, R., et al., Eur. J. Biochem: v104, p 469-478 (1980).
4. Hsu C H, Chen C, Irimia D, Toner M. Fast sorting of CD4+ T cells from whole blood using glass microbubbles. Technology (Singap World Sci). 2015 March; 3(1):38-44.
5. Liou Y R, Wang Y H, Lee C Y, Li P C. Buoyancy-activated cell sorting using targeted biotinylated albumin microbubbles. PLoS One. 2015 May 20; 10(5).
6. Shi G, Cui W, Mukthavaram R, Liu Y T, Simberg D. Binding and isolation of tumor cells in biological media with perfluorocarbon microbubbles. Methods. 2013 Dec. 1; 64(2):102-7.
7. Shi G, Cui W, Benchimol M, Liu Y T, Mattrey R F, Mukthavaram R, Kesari S, Esener S C, Simberg D. Isolation of rare tumor cells from blood cells with buoyant immuno-microbubbles. PLoS One. 2013; 8(3).
8. Clarke, J., Braginski, A. I., v1, SQUID Handbook; ISBN#3-527-40229-2; (2004); Berlin:Wiley-VCH.
9. Miltenyi et al., Cytometry: v11, p 231-238 (1990)
10. Kevin R, et al. Magnetic particle detection (MPD) for in-vitro dosimetry, Biosensors and Bioelectronics Volume 43, 15 May 2013, Pages 88-93

All of the compositions, articles, devices, systems, and methods disclosed and claimed herein can be made and executed without undue experimentation in light of the present disclosure. While the compositions, articles, devices, systems, and methods of this invention have been described in terms of preferred embodiments, it will be apparent to those of skill in the art that variations may be applied to the compositions, articles, devices, systems, and methods without departing from the spirit and scope of the invention. All such variations and equivalents apparent to those skilled in the art, whether now existing or later developed, are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims, which may also contain even further embodiments of the invention.

What is claimed is:

1. A targeted nanomagnetic particle, comprising:
    (a) a magnetic core particle;
    (b) a glass layer encapsulating the magnetic core particle;
    (c) a protein/polymer composite layer bound to the glass layer, wherein the protein/polymer composite layer i) comprises serum albumin and ii) is covalently bound to the glass layer; and
    (d) a targeting moiety that comprises one member of a bioaffinity ligand pair covalently conjugated to the serum albumin in the protein/polymer composite layer, wherein the targeted nanomagnetic particle has a diameter ranging from about 30 nm to about 300 nm.

2. A targeted nanomagnetic particle according to claim 1, wherein the magnetic core particle comprises a ferrous oxide; a chromium oxide; or a stable metal oxide that comprises a substituted metal ion selected from the group consisting of Mn, Co, Ni, Zn, Gd, and Dy.

3. A targeted nanomagnetic particle according to claim 1, wherein the glass layer is a silane layer formed from organofunctional alkoxysilane molecules.

4. A targeted nanomagnetic particle according to claim 1, wherein the targeting moiety is selected from the group consisting of an antibody, an antigen-binding antibody fragment, a cell surface receptor, a ligand-binding extracellular domain of a cell surface receptor, a nucleic acid, avidin, streptavidin, and biotin.

5. A targeted nanomagnetic particle according to claim 1 that further comprises a detectable label.

6. A targeted nanomagnetic particle according to claim 2, wherein the magnetic core particle comprises magnetite ($Fe_3O_4$) crystals.

7. A composition comprising a plurality of targeted nanomagnetic particles according to claim 1.

8. A composition according to claim 7 that is a dry and readily dispersible or liquid composition.

9. A composition according to claim 7, wherein the plurality of targeted nanomagnetic particles comprises a plurality of targeted nanomagnetic particle species, wherein each targeted nanomagnetic particle species comprises a different targeting moiety species.

10. A kit comprising a composition according to claim 7 in a container and instructions for use of the composition.

11. A targeted nanomagnetic particle according to claim 6, wherein the magnetite crystals have a diameter ranging from about 5 nm to about 300 nm.

12. A targeted nanomagnetic particle according to claim 3, wherein the organofunctional alkoxysilane molecules comprise a couplable end group.

13. A targeted nanomagnetic particle according to claim 12, wherein the couplable end group is selected from the group consisting of an amino, sulphydryl, carboxyl, and hydroxyl end group.

14. A targeted nanomagnetic particle according to claim 1, wherein the protein/polymer composite layer further comprises one or more of dextran and casein.

15. A targeted nanomagnetic particle according to claim 1, wherein the serum albumin comprises bovine serum albumin or human serum albumin.

16. A targeted nanomagnetic particle according to claim 1, wherein the protein/polymer composite layer is permanently bound by heating to a temperature from about 45° C. to about 85° C.

17. A targeted nanomagnetic particle according to claim 2, wherein the ferrous oxide is $Fe_3O_4$ or $Fe_2O_3$.

18. A targeted nanomagnetic particle according to claim 2, wherein the chromium oxide is $CrO_3$.

* * * * *